United States Patent
Barnes

(10) Patent No.: US 9,358,148 B2
(45) Date of Patent: Jun. 7, 2016

(54) DIP JOINT EXTENSION SPLINT AND METHODS OF USING SAME

(71) Applicant: Annulus LLC, Austin, MN (US)

(72) Inventor: Darryl E. Barnes, Austin, MN (US)

(73) Assignee: Annulus, LLC, Byron, MN (US)

( * ) Notice: Subject to any disclaimer, the term of this patent is extended or adjusted under 35 U.S.C. 154(b) by 373 days.

(21) Appl. No.: 13/827,903

(22) Filed: Mar. 14, 2013

(65) Prior Publication Data

US 2013/0261524 A1    Oct. 3, 2013

Related U.S. Application Data

(60) Provisional application No. 61/619,697, filed on Apr. 3, 2012.

(51) Int. Cl.
  *A61F 5/00* (2006.01)
  *A61F 5/01* (2006.01)
  *A61F 5/058* (2006.01)

(52) U.S. Cl.
  CPC ............... *A61F 5/013* (2013.01); *A61F 5/0118* (2013.01); *A61F 5/05866* (2013.01); *A61F 5/05875* (2013.01)

(58) Field of Classification Search
  CPC ... A61F 5/013; A61F 5/0585; A61F 5/05875; A61F 5/50; A61B 17/6425; A61B 17/66
  USPC ............. 602/5, 21, 22, 30; 2/21, 22; 128/879, 128/880; D24/189
  See application file for complete search history.

(56) References Cited

U.S. PATENT DOCUMENTS

| | | | |
|---|---|---|---|
| 1,917,794 A | | 7/1933 | Brown |
| 2,548,378 A | * | 4/1951 | Kleinfeld .................. 602/22 |
| 2,573,715 A | | 11/1951 | Leroy |
| 2,646,794 A | | 7/1953 | Baer |
| 3,938,510 A | | 2/1976 | Gerber |
| 4,932,396 A | | 6/1990 | Garris |
| 5,077,870 A | | 1/1992 | Melbye et al. |
| 5,417,692 A | | 5/1995 | Goble et al. |
| 5,752,926 A | | 5/1998 | Larson et al. |
| 5,807,291 A | | 9/1998 | Larson et al. |
| 5,925,008 A | | 7/1999 | Douglas |
| 6,076,238 A | | 6/2000 | Arsenault et al. |
| 6,110,136 A | | 8/2000 | Belkin |
| 6,692,435 B1 | | 2/2004 | Choate |
| 6,692,452 B2 | | 2/2004 | Chow |
| 6,716,186 B1 | | 4/2004 | Singh et al. |
| 6,808,502 B2 | | 10/2004 | Nguyen |

(Continued)

OTHER PUBLICATIONS

"A Patient's Guide to Mallet Finger Injuries," Montana Spine and Pain Center, EOrthopod, Medical Multimedia Group, LLC, retrieved from the Internet Aug. 9, 2007: URL:http://www.eorthopod.com/eorthopodV2/index/php/fuseaction/topics . . . ; 4 pages.

(Continued)

*Primary Examiner* — Kim Lewis
(74) *Attorney, Agent, or Firm* — Patterson Thuente Pedersen, P.A.

(57) ABSTRACT

Finger splints for use in connection with distal interphalangeal (DIP) joint fractures are disclosed. The splints include a ring element at least partially positioned around a finger at a location proximal to the distal interphalangeal (DIP) joint and include an extension member that extends over the DIP joint and attaches to the fingernail.

27 Claims, 15 Drawing Sheets

(56) References Cited

U.S. PATENT DOCUMENTS

| | | | |
|---|---|---|---|
| D515,216 S | 2/2006 | Weber et al. | |
| 7,041,106 B1 | 5/2006 | Carver et al. | |
| 7,914,474 B2 | 3/2011 | Barnes | |
| 8,128,586 B2* | 3/2012 | Barnes | A61F 5/05875 602/20 |
| 2006/0206047 A1* | 9/2006 | Lampe et al. | 602/42 |
| 2009/0099493 A1* | 4/2009 | Barnes | A61F 5/05875 602/22 |
| 2009/0204044 A1* | 8/2009 | Benison | A61F 5/05875 602/22 |

OTHER PUBLICATIONS

"Buddy Taping," How to Describe an Injury, retrieved from the Internet Aug. 9, 2007: URL:http://www.siumed.edu/surgery/ortho/residents/injury.htm . . . ; 1 page.

"Conditions. Mallet Finger. Mallet (Baseball) Finger," 3 Point Products, © 2005, retrieved from the Internet Aug. 9, 2007: URL:http://www.3pointproducts.com/index.asp?pageid+3&conditionid+21 . . . ; 2 pages.

Mallet Finger ("Baseball Finger" or "Extensor Tendon Injury"), © 2000 DynoMed.com, retrieved from the Internet Aug. 9, 2007: URL:http://www.dynomed.com/encyclopedia/encyclopedia/hand_and wri . . . ; 2 pages.

"Products. Oval-8® Finger Splint," 3 Point Products, © 2005, retrieved from the Internet Aug. 9, 2007: URL:http://www.3pointproducts.com/index.asp?productid+43&pageid_2 . . . ; 2 pages.

"Products. Hand&Finger,"Medex medical Supplies Ltd., retrieved from the Internet Aug. 9, 2007: URL:http://www.medex.com.hk/gb/enpart/hand.htm . . . : 2 pages.

Rehak D.C., "Finger Injuries in Basketball Players," Hughston Health Alert,, retrieved from the Internet Aug. 9, 2007: URL:http://www.hughston.com/hha/a_16_4_2.htm . . . ; 2 pages.

Application and File History of U.S. Appl. No. 12/244,084, Inventor Barnes, filed Oct. 2, 2008.

Application and File History of U.S. Appl. No. 13/029,319. Inventor Barnes, filed Feb. 17, 2011.

* cited by examiner

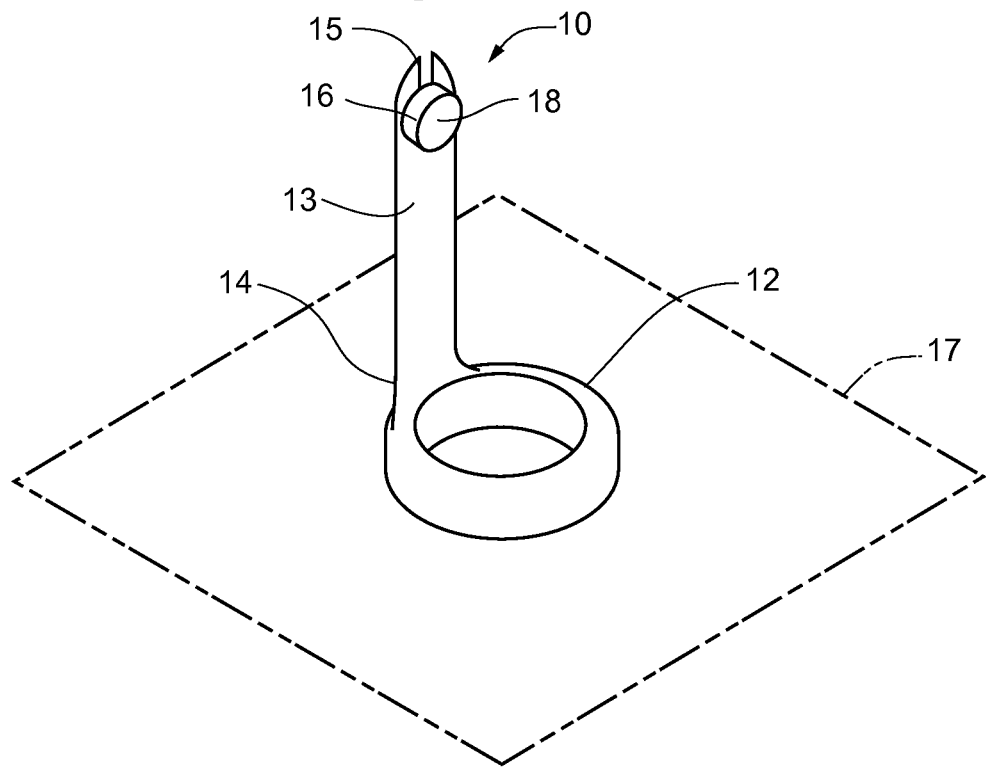
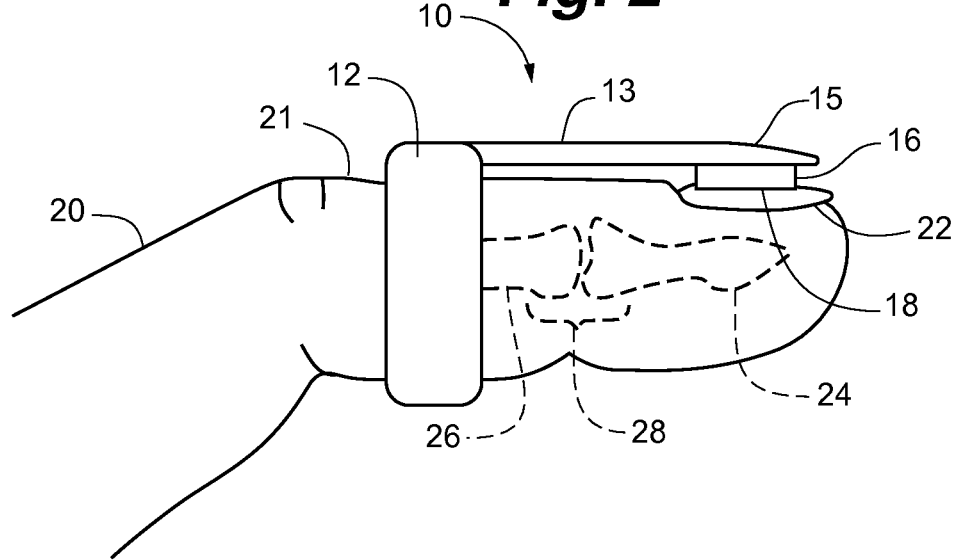

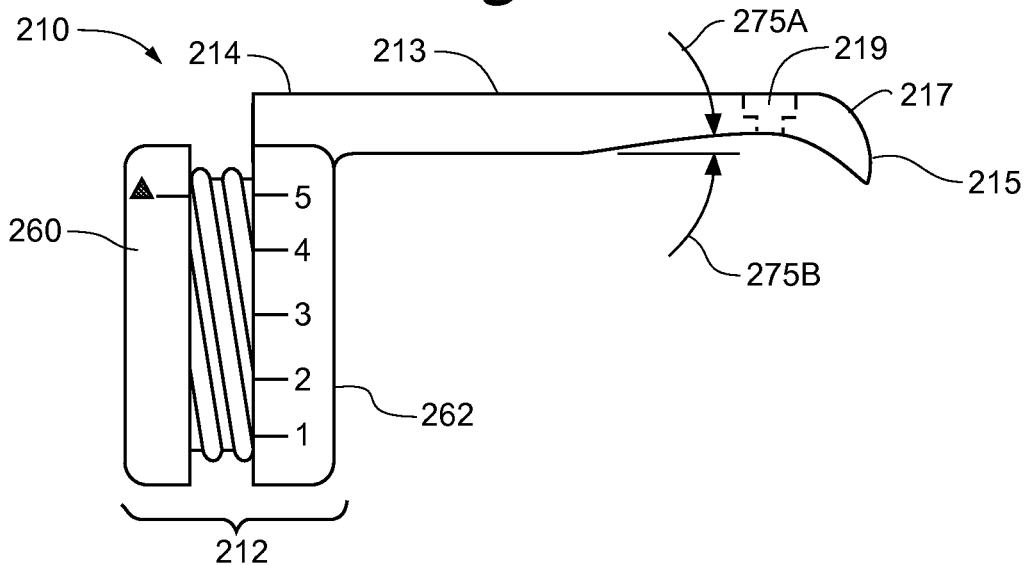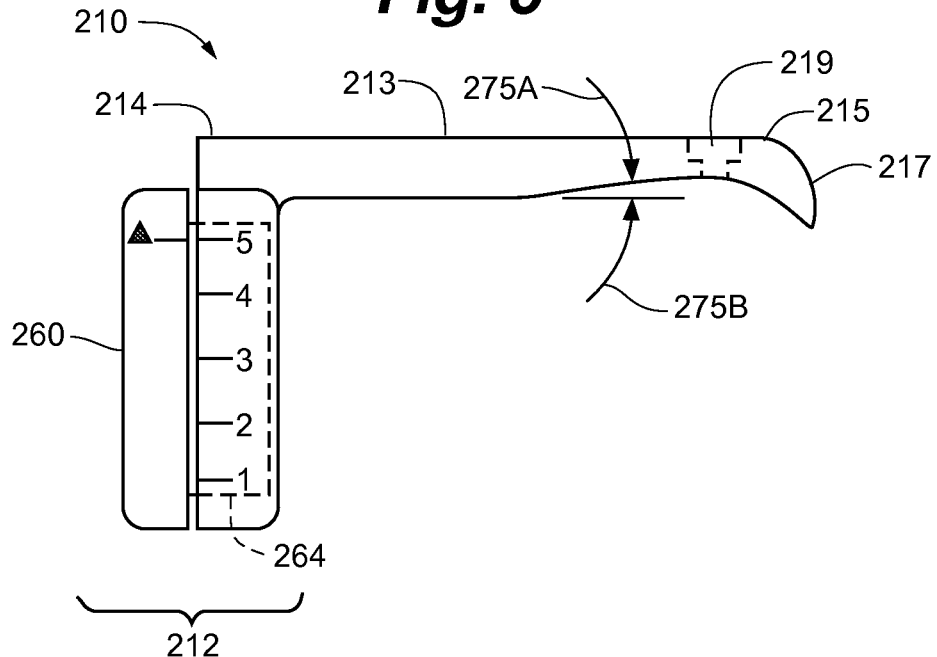

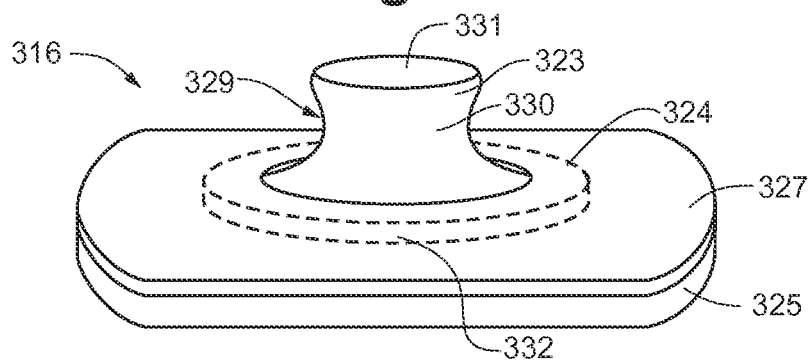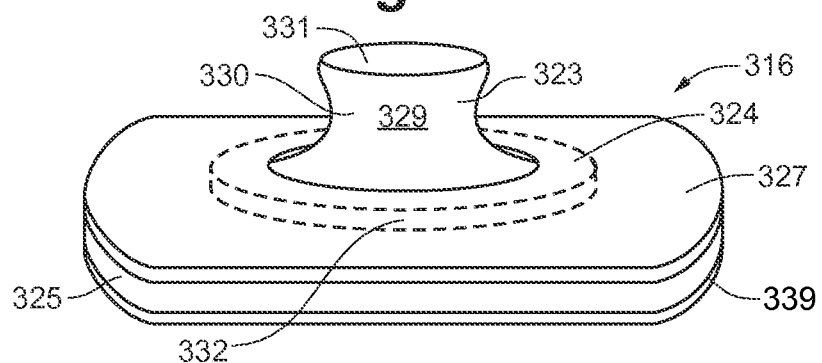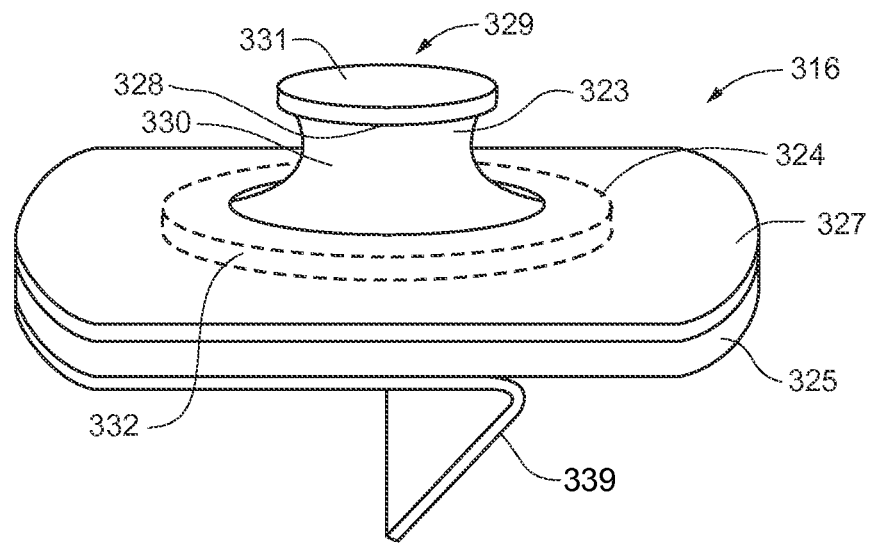

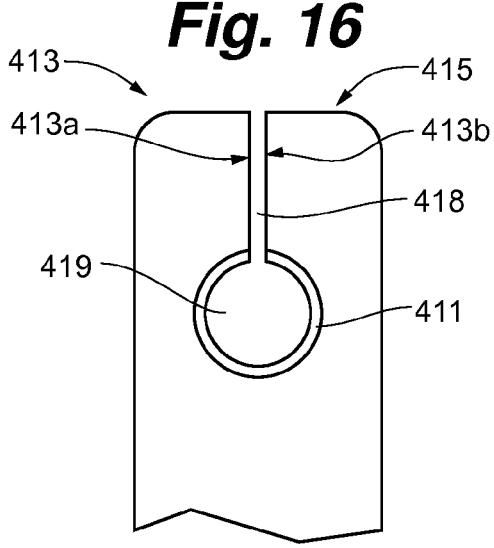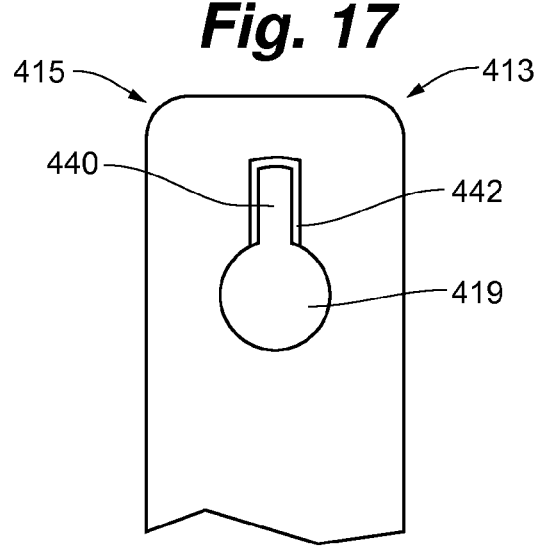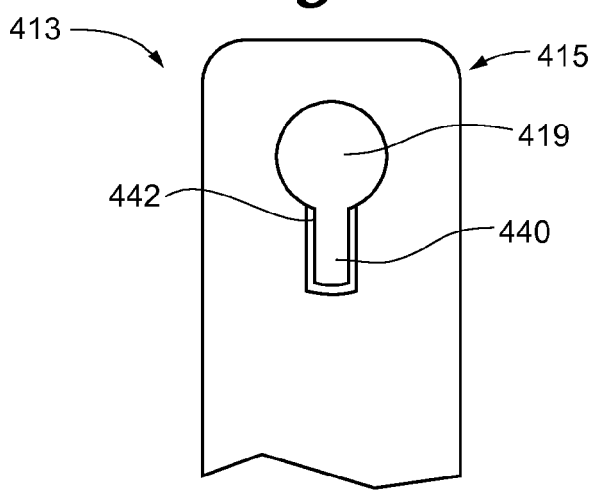

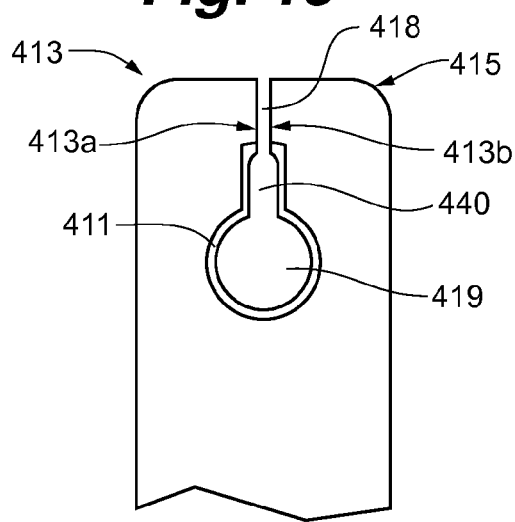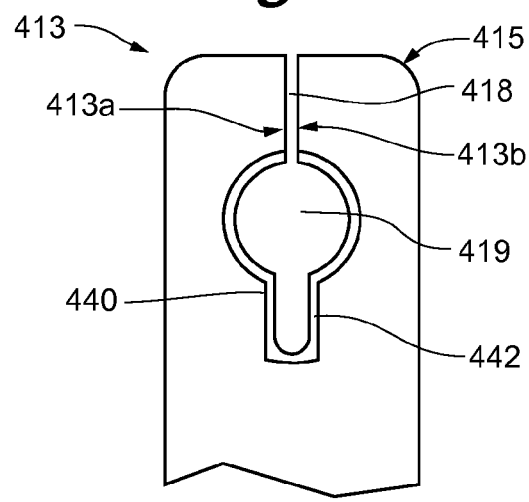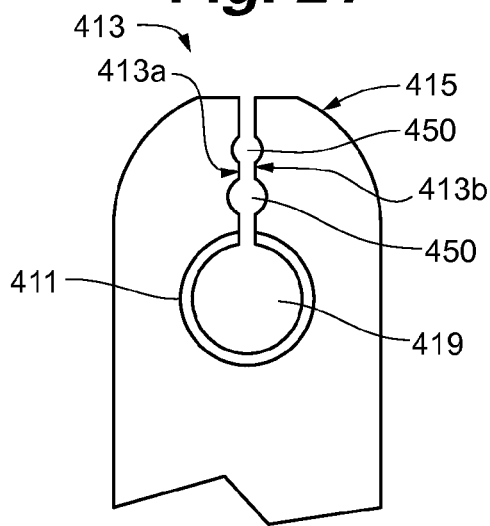

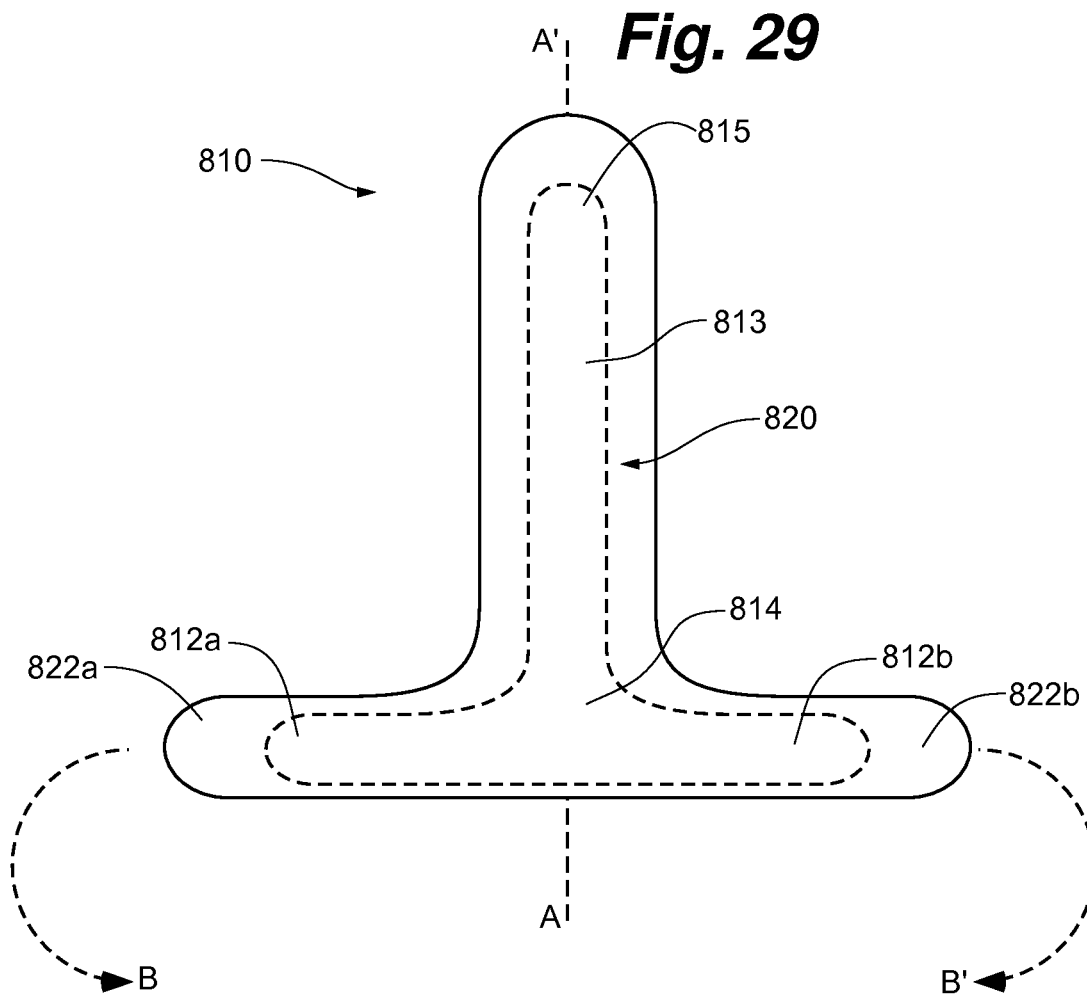
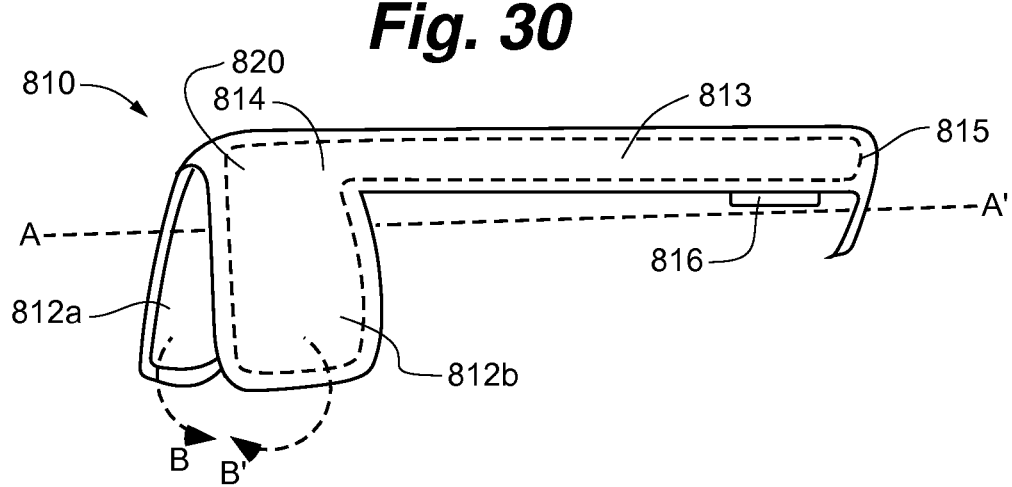

DIP JOINT EXTENSION SPLINT AND METHODS OF USING SAME

RELATED APPLICATION

The present application claims the benefit of U.S. Provisional Application No. 61/619,697, filed Apr. 3, 2012, which is incorporated herein in its entirety by reference.

FIELD OF THE INVENTION

The present invention relates to a finger splint. More particularly, the present invention relates to a distal interphalangeal (DIP) joint extension splint.

BACKGROUND OF THE INVENTION

A splint is a device used for immobilization or holding a part of the body stable to facilitate healing and protect a wounded body part from further damage. A variety of injuries can be treated with splints, including injuries to fingers such as breaks, fractures, strains and sprains. One such injury is "Mallet Finger," which may occur when a force is directed at the distal finger resulting in an avulsion of the extensor tendon from the dorsum of the base of the distal phalanx. Currently, there are several splints on the market that are used to treat this injury. Compared to more permanent solutions such as a cast, splints are often used for immobilizing an injured finger to allow for adjustment, removal, and replacement of the splint as desired.

For example, medical personnel may apply a splint to a freshly injured finger, which may have associated swelling. As the swelling subsides, the splint may be adjusted to maintain a proper fit. The splint may also need to be removed temporarily for therapy as the injury heals or is in the process of healing. Patient compliance, however, is also an issue that may affect the outcome after treating these types of finger injuries, e.g., "Mallet Finger." In many cases, the splint should be left in place for 6-8 weeks without removal. Many patients, however, remove these splints before the injury has completely healed for several reasons, e.g., not knowing that the splint should stay in place for 6-8 weeks, to wash their injured finger, to adjust the splint for a more/less snug fit, etc. Early removal of the splint may result in failed healing and/or deformity.

U.S. Pat. No. 7,914,474 and U.S. Pat. No. 8,128,586, which are hereby incorporated by reference in their entirety, are directed at finger splints for use in the treatment of finger injuries that properly immobilize an injured finger while still allowing for adjustment, removal, and replacement of the splint as desired.

However, there still remains a need for improved finger splints that properly immobilize an injured finger while still allowing for adjustment, removal, and replacement of the splint as desired. There is also a need for an improved finger splint that allows for adequate washing of the injured finger without the need for early removal of the splint that may result in failed healing and/or deformity.

SUMMARY OF THE INVENTION

Applicant has invented a substantial improvement for finger splints described and claimed in the above-identified patents that properly immobilize an injured finger while still allowing for adjustment, removal, and replacement of the splint as desired.

According to certain aspects of the present invention, a splint may include a ring element positioned at least partially around a finger at a location proximal to the distal interphalangeal (DIP) joint, an extension member connected to the ring element and extending over the DIP joint between the ring element and the fingernail, the extension member proximate the fingernail end having an aperture for operably receiving a protruding portion of an attachment element that can be operably coupled to the fingernail. In certain aspects, the attachment element is operably coupled to the fingernail by an adhesive.

The extension member is preferably positioned only over the top surface of the finger. Doing so may result in increased compliance because the patient retains use of the finger tip sensation and is preferably able to wash the finger without removing the splint. Further, in certain aspects, tape may not need to be used to hold the splint on the finger, which may reduce the possibility of allergic reaction to the adhesive where it contacts the patient's skin. In other aspects, tape or other adhesive, binding or fastening material may be utilized to hold two ring tab portions in a ring element configuration at least partially around a finger.

In certain aspects, the present invention provides a finger splint for use in the treatment of finger injuries, the splint including a ring element sized to fit at least partially around a finger at a location proximal to the distal interphalangeal (DIP) joint; an extension member having a proximal end attached to the ring element, a distal end located distally from the ring element, and an aperture proximate the distal end; and an attachment element having a protruding portion capable of operably engaging within the aperture on the extension member; wherein the attachment element is capable of operably coupling the extension member to a fingernail when the ring element is positioned at least partially around the finger.

In certain aspects, the protruding portion of the attachment element has a proximal end proximately located an attachment pad and a distal end having a substantially circular shape having a first diameter, and the aperture within the extension member having a circular shape having a second diameter, wherein the first diameter is slightly larger than the second diameter such that the distal end of the protruding portion is capable of mechanically slip fitting within the aperture to mechanically fasten the attachment element to the extension member.

In certain aspects, the protruding portion of the attachment element has an intermediately located extension section between the distal end and the proximal end, the intermediately located extension section having a smaller diameter than the diameter of the distal end defining a shoulder proximate the distal end. When the distal end of the protruding portion of the attachment element is pressed into the aperture of the extension member, the distal end passes through the aperture and the intermediately located extension section is operably engaged within the aperture such that the outer perimeter of the intermediately located section operably engages within the inner cross sectional portion of the aperture located on the extension member and the shoulder may also operably engage the top side of the extension member or a recessed portion of the extension member proximate the aperture. In certain aspects, the extension member has a partial aperture or recess with a diameter larger than the diameter of the aperture defining a shoulder portion, such that the shoulder portions of the protruding portion and the recessed aperture operable engage each other when the attachment element is operably coupled to the extension member.

In certain aspects, the extension member has a slit connected to the aperture located between the aperture and the distal end defining a first side and a second side on the distal end of the extension member, such that the diameter of the aperture is capable of being increased when a rotatable axial force is applied proximate the slit that pushes the first and second distal end sides away from each other. In certain aspects, the diameter of the aperture is capable of being increased when a force is applied proximate the slit, pushing the first and second distal end sides away from each other.

In certain aspects, the extension member has a slot connected to the aperture located between the aperture and the proximal end, such that the distal end of the protruding portion is capable of being inserted within the aperture and then the attachment element capable of being operably coupled to the extension member in a stabilizing position by sliding the intermediately located section within the slot in a direction towards the proximal end of the extension member. In certain aspects, the slot has a width that is narrower than the diameter of the aperture but wide enough to receive the intermediately located section of the protruding portion.

In certain aspects, the extension member has a slot connected to the aperture located between the aperture and the distal end, such that the distal end of the protruding portion is capable of being inserted within the aperture and then the attachment element capable of being operably coupled to the extension member in a stabilizing position by sliding the intermediately located section within the slot in a direction towards the distal end of the extension member. In certain aspects, the slot has a width that is narrower than the diameter of the aperture but wide enough to receive the intermediately located section of the protruding portion.

In certain aspects, the splint may include one or more of the following features: the extension member may define an extension member axis between the proximal end and the distal end of the extension member, and the distance between the attachment element and the ring element along the extension member axis is adjustable; the finger splint may position the finger or a finger in hyperextension; the attachment element may include adhesive for attachment to a fingernail on which the splint is mounted; the extension member may be adjustably attached to the ring element such that the distance between the distal end of the extension member and the ring element can be adjusted proximate the ring element; the ring element may be a closed member; the ring element may be in the form of a slot; the distal end of the extension member may have a concave surface shaped to receive a fingertip; the ring element may be in the form of a male portion and a female portion, wherein the male portion and the female portion screw together; the ring element may include a tab and ratchet mechanism; and/or the ring element configuration may be achieved by bending two ring tab portions at least partially around the finger and secured in place, such as by an adhesive material interconnecting the two ring tab portions.

In certain aspects, the present invention provides a finger splint for use in the treatment of finger injuries, the splint including a ring element sized to fit at least partially around a finger at a location proximal to the distal interphalangeal (DIP) joint, the ring element comprising two opposed bendable or flexible ring portions that can be bent to be configured into the ring element; an extension member having a proximal end attached to the ring element and a distal end located distally from the ring element; and an attachment element capable of operably coupling the extension member to a fingernail when the ring element is positioned at least partially around a finger. In some aspects, the two opposed bendable ring portions are held at least partially around the finger and in a ring element configuration by tape or other adhesive material. In some aspects, a soft cover material overlays the bendable ring portions and/or the extension member. In some aspects, the soft cover material is an adhesive material that attaches directly to the flexible ring portions and/or the rigid extension member. In some aspects, the soft cover material overlaying the flexible ring portions is utilized to hold the flexible ring portions into a ring element configuration during use. In some aspects, the ring portions will revert to their original position when not held at least partially around a central axis, such as a finger. In some aspects, the ring portions and the extension member are at least partially in the same plane when the ring portions are not at least partially bent to form a ring element configuration. In some aspects, the ring elements are bent around a central axis, such as a finger, and overlap with each other to form the ring element configuration.

In some aspects of the present invention, a finger splint for use in the treatment of finger injuries, comprises a ring element sized to fit at least partially around a finger at a location proximal to the distal interphalangeal (DIP) joint, the ring element comprising two opposed flexible ring portions; an extension member having a proximal end attached to the ring element and a distal end located distally from the ring element; and an attachment element capable of operably coupling the extension member to a fingernail when the ring element is positioned at least partially around a finger. In some aspects, the finger splint has a T-shaped configuration, which provides for ease of packaging the device in flat configuration. In some aspects, the two opposed bendable ring portions are bent at least partially around the finger into a ring element configuration, the bendable ring portions held in the ring element configuration by an adhesive material, such as tape or an adhesive overlay material. In some aspects, the two opposed bendable ring portions contain a different overlay material that is utilized to hold the bendable ring portions into a ring element configuration at least partially around the finger. In some aspects, the overlay material contains an adhesive material proximate the end areas of the bendable ring portions. In some aspects, the overlay material contains hook and fasten type material proximate the end areas of the bendable ring portions, such as Velcro®.

In some aspects of the present invention, the overlay material extends at least partially the length of the extension element, in other aspects the entire length of the extension element, and in other aspects a length exceeding the extension element. In some aspects, the overlay material is wider than the width of the extension element, such that the overlay material can operably interact with the finger. In some aspects, the overlay material comprises an adhesive material that allows the bendable ring portions to be configured into a ring element at least partially around the finger, the overlay material may be adhered at least partially to the finger intermediate the proximal end and the distal end of the extension member, and/or the overlay material extends over the distal end of the attachment element such that the adhesive overlay material can attach at least partially to the finger tip.

In another aspect, the present invention may provide a method of restraining a finger, the method including locating a splint on a finger, wherein the splint includes a ring element positioned proximally from the distal interphalangeal joint and an attachment element positioned adjacent a fingernail of the finger, with an extension member connecting the attachment element to the ring element; and operably attaching a protruding portion of the attachment element of the splint within an aperture of the extension member while the ring element is positioned on the finger and the attachment element is positioned on the fingernail.

In another aspect, the present invention may provide a method of restraining a finger, the method including locating a splint on a finger, wherein the splint includes flexible ring portions, the flexible ring portions bendable into a ring element that is capable of being positioned proximally from the distal interphalangeal joint and an attachment element positioned adjacent a fingernail of the finger, with an extension member connecting the attachment element to the ring element. In some aspects, the splint comprises an overlay material, the overlay material allowing the flexible ring portions to be retained in a ring element configuration. In some aspects, the overlay material also extends over the width of the extension member such as to hold the extension member to the length of the finger and/or extending over the distal end of the extension member such that the overlay material at least partially adheres to the finger tip.

In another aspect, the present invention provides a finger splint for use in the treatment of finger injuries, the splint including a ring element sized to fit over at least a portion of a middle phalanx of a finger, wherein the ring element defines a finger axis; an extension member extending along and aligned with the finger axis between a proximal end and a distal end, wherein the extension member is attached to the ring element at the proximal end of the extension member; and an attachment element is capable of being mechanically attached to the extension member proximate the distal end of the extension member by a mechanical snap configuration between the attachment element and the extension member, wherein the attachment element is located between the extension member and a fingernail of the finger. The attachment element is optionally adjustably attached to the extension member such that the distance between the ring element and the attachment element is adjustable.

In another aspect, the finger splints of the present invention may include an extension member that defines an extension member axis, wherein a position of the attachment element is adjustable within a slot portion along the extension member axis. The extension member may include an aperture connected to the slot portion proximate the distal end of the extension member, and the position of the attachment element is adjustable within the slot portion. The aperture of the extension member may operably receive a distal end of a protruding portion of the attachment element, and an intermediately located section of the protruding portion may be operably slidably adjustable within the slot portion.

In certain aspects, the finger splints of the present invention may include one or more of the following features: the finger splint may position a finger in hyperextension; the finger splint may position a finger in about 2-5 degrees of hyperextension, in some aspects about 3 degrees of hyperextension; the adhesive may be pressure sensitive adhesive; the extension member may be adjustably attached to the ring element such that the distance between the distal end of the extension member and the ring element can be adjusted proximate the ring element; the extension member and the ring element may be a one piece, completely integral molded polymer article; the ring element may be a closed member; the ring element may include a slot for variable ring size; the ring element may comprise two ring tab portions made from a flexible material that allows the ring tab portions to be bent at least partially around the finger to obtain a ring element configuration; the length of the ring element may be adjustable; the distal end of the extension member may include a concave surface shaped to receive a fingertip; and the ring element may include a male portion and a female portion, wherein the male portion and the female portion screw together.

In certain aspects, the ring elements of the present invention may include an inner portion that comes in contact with the skin and an outer portion, wherein the inner portion and the outer portion comprise different materials. In some aspects, the inner portion includes a material that has a shore hardness that is less than the outer portion. In some aspects, the material of the inner portion is directly connected to the material of the outer portion by overlay molding. In some aspects, the material of the inner portion is connected to the material of the outer portion by an intermediate adhesive. In some aspects, the inner portion comprises a soft cushion-like material, such as a foam, cloth material, gel or the like. In some aspects, the inner portion comprises a wicking material, such as Gortex®, that facilitates the removal of moisture from the skin.

In another aspect, the present invention may provide a method of restraining a finger by locating a splint according to certain aspects of the present invention on a finger, positioning the ring element of the splint proximally the distal interphalangeal joint, attaching the attachment element to a fingernail of the finger; and coupling the attachment element of the splint to the distal end of the extension member of the splint by snapping a protruding portion of the attachment element oppositely opposed the fingernail attachment surface into an aperture proximally the distal end of the extension member. The attachment element may be attached to the fingernail by an adhesive.

In another aspect, the present invention may provide a method of restraining a finger by locating a splint according to certain aspects of the present invention on a finger, positioning the ring element of the splint proximally the distal interphalangeal joint, attaching the attachment element to a fingernail of the finger; and coupling the attachment element of the splint to the distal end of the extension member of the splint by magnetically attaching a protruding portion of the attachment element oppositely opposed the fingernail attachment surface to the distal end of the extension member. The attachment element may be attached to the fingernail by an adhesive.

These and other features and aspects of the present invention may be described below in connection with some exemplary embodiments of the invention and other attributes and benefits of the foregoing will be apparent to one of ordinary skill in the art from the following drawings and detailed description.

BRIEF DESCRIPTION OF THE DRAWINGS

FIG. 1 depicts a perspective and illustrative view of one exemplary finger splint according to the present invention.

FIG. 2 is a side view of the splint of FIG. 1 in place on the DIP joint of a finger.

FIG. 5 is a side view of another exemplary splint according to the present invention.

FIG. 6 is a side view of the splint of FIG. 5 with the male section of the ring element threaded within the female section.

FIG. 13 is a side perspective view of an exemplary attachment element according to the present invention, the attachment element having a side for operably engaging a fingernail and a protruding member for operably engaging the extension member.

FIG. 14 is a side perspective view of the exemplary embodiment of FIG. 13 with a removable layer covering the fingernail attachment surface of the attachment element.

FIG. 15 is a side perspective view of an exemplary attachment element according to the present invention with a removable layer covering the fingernail attachment surface of the attachment element partially removed to partially expose the fingernail attachment surface, and the protruding member having a distal end configuration that provides a shoulder portion.

FIG. 16 is a top plan view of an exemplary extension member portion of a splint according to the present invention, the extension member having a slit connected to an aperture and extending to the distal end of the extension member of the splint.

FIG. 17 is a top plan view of an exemplary extension member portion of a splint according to the present invention, the extension member having a slot connected to an aperture, the slot proximally located between the aperture and the distal end of the splint.

FIG. 18 is a top plan view of an exemplary extension member portion of a splint according to the present invention, the extension member having a slot connected to an aperture, the slot proximally located between the aperture and the ring element of the splint.

FIG. 19 is a top plan view of an exemplary extension member portion of a splint according to the present invention, the extension member having a slit connected to an aperture via an intermediately located slot portion with the slot located between the aperture and the distal end of the splint and the slit extending to the distal end of the extension member.

FIG. 20 is a top plan view of an exemplary extension member portion of a splint according to the present invention, the extension member having a slit connected to an aperture and extending to the distal end of the extension member, and a slot connected to the aperture and located between the aperture and the proximal end of the extension member.

FIG. 21 is a top plan view of an exemplary extension member portion of a splint according to the present invention, the extension member having a slit connected to an aperture and extending to the distal end of the extension member, the slit having two intermediately located expansion key receiving apertures.

FIG. 29 is a top plan view of an exemplary splint according to the present invention, the splint having a substantially flat configuration prior to being applied to a finger, the splint having flexible ring portions that are capable of being bent at least partially around a central axis, which in operation comprises a finger, to form a ring element configuration. The dotted lines representing an underlying material of the ring portions and extension member of the splint located underneath the overlay material in this top plan view.

FIG. 30 is a perspective view of the exemplary splint of FIG. 29 with the flexible ring portions partially bent around a central axis represented by line A-A', and the overlay material extending past the flexible ring portions and the distal end of the extension member.

Figure 3:
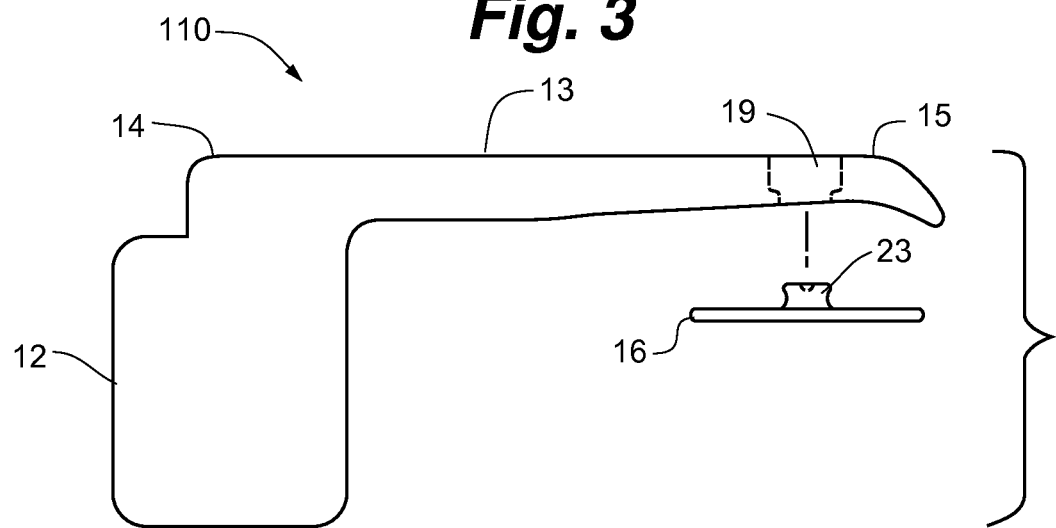
FIG. 3 is a side view of another exemplary splint according to the present invention.

While the present invention is amendable to various modifications and alternative forms, specifics thereof have been shown by way of example in the drawings and will be described in further detail below. It should be understood, however, that the intention is not to limit the present invention to the particular exemplary embodiments described. On the contrary, the intention is to cover all modifications, equivalents, and alternatives falling within the spirit and scope of the present invention as defined by the appended claims.

DETAILED DESCRIPTION OF THE DRAWINGS

In the following detailed description of illustrative embodiments of the present invention, reference is made to the accompanying drawings which form a part hereof, and in which are shown, by way of illustration, specific embodiments in which the present invention may be practiced. It is to be understood that other embodiments may be utilized and structural changes may be made without departing from the spirit and scope of the present invention.

The words "preferred" and "preferably" refer to embodiments of the present invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present invention.

As used herein, "a," "an," "the," "at least one," and "one or more" are used interchangeably. The term "and/or" (if used) means one or all of the identified elements/features or a combination of any two or more of the identified elements/features.

FIGS. 1 and 2 depict a perspective and illustrative view of one exemplary finger splint according to the present invention. The finger splint 10 may include a ring element 12, an extension member 13, and an attachment element 16.

The ring element 12 may be a solid, continuous cylinder as depicted, which is generally sized to fit over the middle phalanx of a finger. At least in one embodiment, the ring element 12 may be adjustable in length (along an axis defined by the finger), diameter, and/or circumference to accommodate different sizes and/or shapes of fingers. Further, at least in one embodiment, the ring element 12 may not be continuous, e.g., the ring element may include a slot or a notch such that the ring element extends less than 360 degrees around the finger. Still further, at least in one embodiment, the ring element 12 may not be circular, e.g., the ring element 12 may be elliptically or otherwise shaped to conform to the shape of a finger. Still further, in at least one embodiment, the ring element 12 may not be solid, e.g., the ring element 12 may be substantially hollow. Still further yet, a ring element configuration may be obtained by bending two flexible ring portions along an axis defined by the finger, which will be described in more detail herein.

In certain aspects, the ring element 12 of the present invention may include an inner portion that comes in contact with the skin of the finger 21 and an outer portion, wherein the inner portion and the outer portion comprise different materials. In some aspects, the inner portion of the ring element 12 includes a material that has a shore hardness that is less than the material of the outer portion. In some aspects, the material of the inner portion of the ring element 12 is directly connected to a different material of the outer portion of the ring element 12 by overlay molding or overmold processes known to one of ordinary skill in the art. In some aspects, the material of the inner portion is connected to the material of the outer portion by an intermediate adhesive. In some aspects, the inner portion comprises a soft cushion-like material, such as a foam, cloth, gel or the like. In some aspects, the inner portion is a wicking material, such as Gortex® or the like, that facilitates the removal of moisture from the skin of the finger 21.

The extension member 13 in the depicted embodiment is a substantially straight member extending from a proximal end 14 to a distal end 15. The proximal end 14 of the extension member 13 is attached to the ring element 12 and the extension member 13 extends to the distal end 15 substantially perpendicular to a plane 17 defined by the ring element 12 (which plane is also substantially perpendicular to a finger axis of a finger on which the ring element is positioned). In this embodiment, the extension member 13 is integral with the ring element 12, i.e., the extension member 13 and the ring element 12 are provided as a one-piece, completely integral article that may be molded or otherwise formed (e.g., machined, sintered, injection molded, stamped, etc.) from any suitable material (e.g., metal, polymer, ceramic, composites, plastics, etc.).

In some embodiments the extension member 13 may not extend from the ring element 12 in a substantially perpendicular direction relative to plane 17, e.g., the extension member may extend from the plane at an angle that is not perpendicular to the plane 17. In other variations, the extension member 13 may include, e.g., multiple bends or may be continuously curved instead of being substantially straight as depicted in FIGS. 1 and 2.

In still other variations, the extension members of finger splints according to the present invention may be malleable such that the orientation of the extension member 13 with respect to the ring element 12 can be adjusted. The malleability may be provided by, e.g., constructing the extension member and/or ring element out of materials such as metals, plastics (potentially thermoplastics that can be heated to increase malleability), etc. Such malleability may also be useful for adjusting the shape of the extension member such that it avoids contact with the finger between the ring element and the fingernail. Such malleability may also be useful in allowing the ring element 12 to be comprised of ring tab portions that can be bent around an axis defined by the finger to provide a ring element configuration.

In the depicted embodiment, the attachment element 16 is attached to the extension member 13 at a fixed, stationary location. The attachment element 16 may, however, be adjustably attached to the extension member 13, i.e., the position of the attachment element 16 relative to the ring element 12 may be adjustable. For example, the extension member 13 and the attachment element 16 may be attached to each other using an adjustment mechanism so that the distance between the attachment element 16 and the ring element 12 may be adjusted. In another alternative, an adjustment mechanism may be located at the juncture between the ring element 12 and the extension member 13 (with the attachment element 16 in a fixed position on the extension member 13). In still another alternative, the adjustment mechanism may be in a form where the length of the extension member 13 is adjustable, e.g., the extension member 13 may have a telescoping structure, etc.

In perhaps its simplest form, the attachment element 16 may be provided as a mass of adhesive that may or may not have a visually discernable thickness (for example, the attachment element may be in the form a thin layer of cyanoacrylate adhesive located between the extension member 13 and the fingernail 22, although other adhesives may be utilized). In other embodiments, the attachment element 16 may have a thickness and a volume as depicted in FIGS. 1 & 2. In such embodiments, the attachment element 16 may be rigid or resilient. For example, the attachment element 16 may include a resilient body that carries the adhesive used to attach the splint to a fingernail or the body of the attachment element 16 may consist essentially of adhesive. If provided as a resilient body, the resilience of the attachment element 16 may provide some compliance between the extension member 13 and the fingernail 22 to which the device is attached.

In certain aspects of the present invention, the attachment element may include a mechanical fastener system that includes two components that mechanically attach to each other. In other certain aspects of the present invention, the attachment element may include a magnetic fastener system that includes two components that magnetically attach to each other. Whether a mechanical fastener system or a magnetic fastener system, it may be preferred that one component be attached or attachable (e.g., adhesively) to the fingernail and also attached or attachable to the second mating component located proximate the distal end of the extension member. Attachment of the two components to each other then serves to attach the fingernail to the extension member.

FIG. 2 depicts a perspective and illustrative view of exemplary splint 10 in position on a finger 20. The bones of the finger 20 are depicted to better illustrate the functionality of the splint 10. More specifically, the finger 20 includes skin 21, a fingernail 22, a distal phalanx 24, a middle phalanx 26, and a distal interphalangeal joint 28. As shown in this depiction, the ring element 12 of the splint 10 is located around the middle phalanx 26 of the finger 20 at a location proximal to the distal interphalangeal joint 28. The extension member 13 extends from the ring element 12 to the tip of the distal phalanx 24. The extension member 13 extends over a top surface of the finger 20, allowing sensation to be retained on the fingertip.

The attachment element 16, as shown, is located near the distal end 15 of the extension member 13 on the side of the extension member 13 facing the interior of the ring element 12. Generally, the attachment element 16 is used to fixedly attach the splint 10 to the fingernail 22 of a finger 20 on which splint 10 is mounted. The surface 18 of the attachment element 16 may preferably be adhered to the fingernail 22. In at least one embodiment, the attachment element 15 may include any suitable adhesive material, e.g., cyanoacrylate, epoxy, acrylic adhesives, etc. It may be preferred that the adhesive be a pressure sensitive adhesive.

The attachment element 16, as shown, is attached to fingernail 22. The attachment element 16 may be used to retain the splint 10 on the finger 20. In turn, the splint 10 may prohibit substantial movement of the distal phalanx 24 at the distal interphalangeal joint 28 as to, e.g., allow an extensor tendon to heal. The adhesive of the attachment element 16 preferably remains selectively attached to the fingernail 22. For example, the adhesive may remain attached for a fixed time period based on average deterioration of the adhesive. Further, for example, the adhesive may remain attached until a releasing compound (e.g., a solvent) is used on the adhesive. Still further, for example, the adhesive may be selected such that it remains attached to the fingernail 22 under a selected amount of force. The selected force may, for example, be greater than the force that a finger may apply to the distal phalanx 24 of that finger.

In at least one embodiment, the splint 10 may secure the distal phalanx 24 in a position that supplies hyperextension, i.e., movement beyond the normal range of motion of the distal phalanx 24 in the dorsal direction. It may be preferred that the splint 10 be capable of securing the distal phalanx 24 in about 2-5 degrees or more, in some aspects about 3 degrees or more of hyperextension. In another characterization, the splint 10 may secure the distal phalanx 24 in some amount of hyperextension up to about, e.g., 5, 10, or even 15 degrees of hyperextension.

Figure 4:
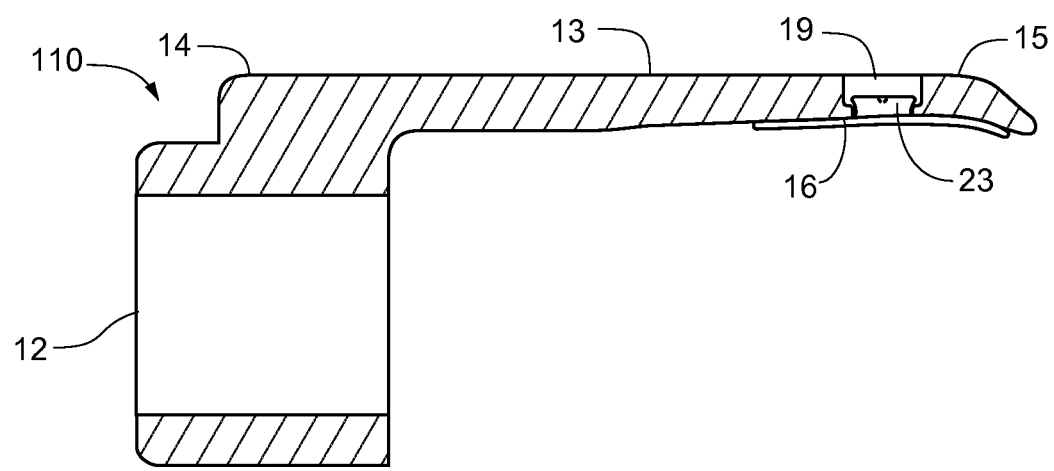
FIG. 4 is a side cross-sectional view of the exemplary embodiment of FIG. 4 with the attachment element operably engaged in an attached position with respect to the extension member.

In certain embodiments, as illustrated in FIGS. 3 and 4, a finger splint 110 includes the extension member 13 proximate the distal end 15 (e.g., corresponding to the fingernail 18 of a patient) having an aperture 19 for operably receiving at least part of a protruding portion 23 of the attachment element 16, which is capable of being operably coupled to the fingernail 22 of a patient. In certain aspects, the attachment element 16 is operably coupled to the fingernail 22 by an adhesive. In certain aspects, the attachment element 16 may include any suitable adhesive material, e.g., cyanoacrylate, epoxy, acrylic adhesives, etc. It may be preferred that the adhesive be a pressure sensitive adhesive. The protruding portion 23 of attachment element 16 may be made of a rigid material with enough pliability such at least part of the protruding portion 23 of attachment element 16 is able to mechanically slip fit or snap into aperture 19, such as illustrated in FIG. 4.

In certain aspects, the protruding portion 23 of the attachment element 16 has a proximal end proximately located an attachment pad and a distal end having a substantially circular shape having a first diameter, and the aperture 19 within the extension member 13 having a circular shape having a second diameter, wherein the first diameter is slightly larger than the second diameter such that the distal end of the protruding portion 23 is capable of mechanically slip fitting within the aperture to mechanically fasten the attachment element to the extension member.

In certain aspects of the present invention, a finger splint 10 for use in the treatment of finger injuries includes a ring element 12 sized to fit at least partially around a finger at a location proximal to the DIP joint; an extension member 13 having a proximal end 14 attached to the ring element 12, a distal end 15 located distally from the ring element 12, and an aperture 19 proximate the distal end 15; and an attachment element 16 having a protruding portion 23 capable of operably engaging within the aperture 19 on the extension member 13; wherein the attachment element 16 is capable of operably coupling the extension member 13 to a fingernail 22 when the ring element 12 is positioned at least partially around a finger 20.

Referring now to FIGS. 5-8, in certain aspects of the present invention provides, a finger splint 210 includes a ring element 212 that is extendable along its longitudinal axis so that when the fingernail of a finger grows and moves the splint 210, the distance between an attachment element 216 and the ring element 212 may be adjusted. The extension member 213 extends from the ring element 212 to the tip of the finger over the top of the finger as to support the joint between the DIP joint. In this embodiment, the extension member 213 extends from the ring element 212 substantially perpendicular to a plane formed through the ring element 212. Near the midsection of the extension member 213, i.e., between the concave portion 217 and the ring element 212, the extension member 213 tapers as to form an angle 275 between 275A and 275B. The angle 275 may be, e.g., greater than zero degrees to about 25 degrees. In this embodiment, the aperture 219 is preferably located between the taper portion that forms the angle 275 and concave portion 217.

Figure 7:
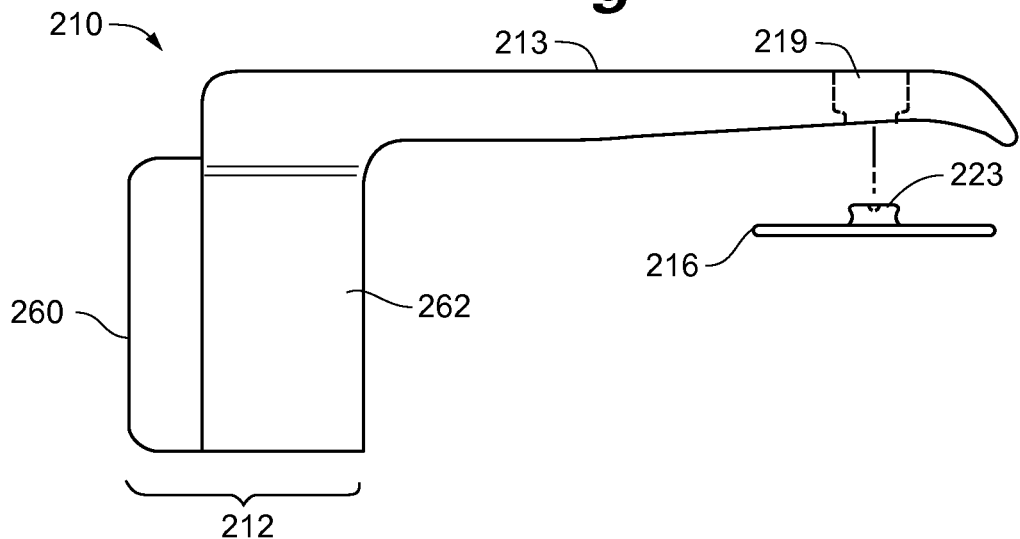
FIG. 7 is a side view of another exemplary splint according to the present invention.
Figure 8:
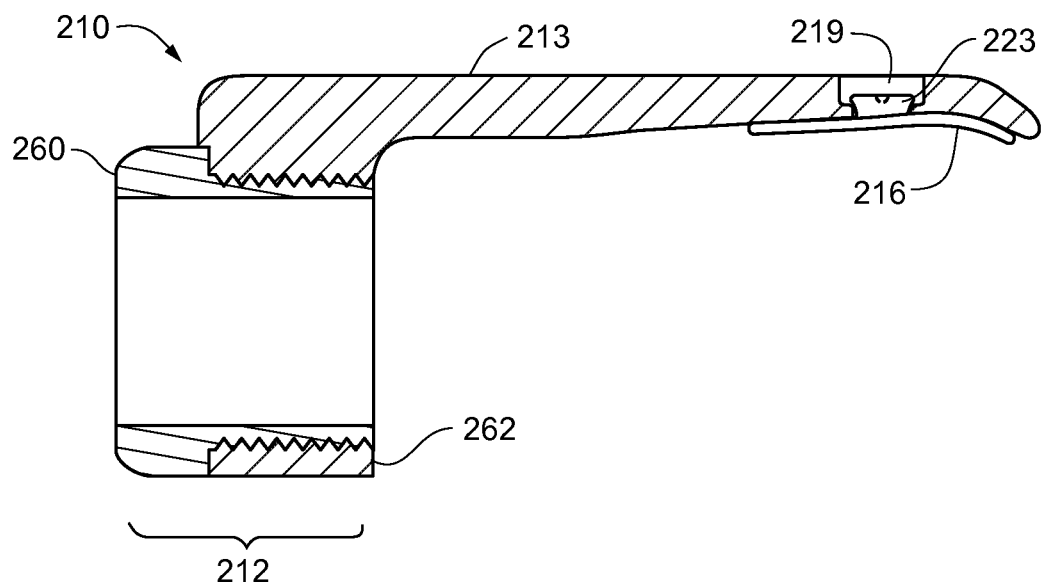
FIG. 8 is a side cross-sectional view of the exemplary embodiment of FIG. 7 with the attachment element operably engaged in an attached position with respect to the extension member and the male section of the ring element threaded within the female section.

In the adjustment mechanism associated with this embodiment, the ring element 212 has two sections: a threaded male section 260 and a threaded female section 262. The male section 260 mates the female section 262 and the inner male section 260 may preferably be positioned proximal to the distal interphalangeal joint to properly position the splint 210. In FIG. 5, the male section 260 is partially unscrewed from the female section 262 as to extend the ring element 212 and increase the distance between the inner male section 260 and the attachment element 216. In FIGS. 6-8, the male section 260 is fully screwed into the female section 262. Dotted line 264 in FIG. 6 signifies where the screw portion of the male section 260 resides within the female section 262, which is similarly shown in the cross-sectional view of the embodiment illustrated in FIG. 8.

As illustrated in FIGS. 5 and 6, the ring element 212 may include indicia on the male section 260 and the female section 262 that correspond with each other as to show a user the distance the male section 260 has been screwed into the female section 262.

The extension member 213 may also have an aperture 219 proximate the distal end 215. As shown in FIGS. 7 and 8, the aperture 219 may operably receive a protruding portion 223 of an attachment element 216, as previously illustrated and discussed with respect to the protruding portion of the attachment element illustrated in FIGS. 3 and 4.

Figure 9:
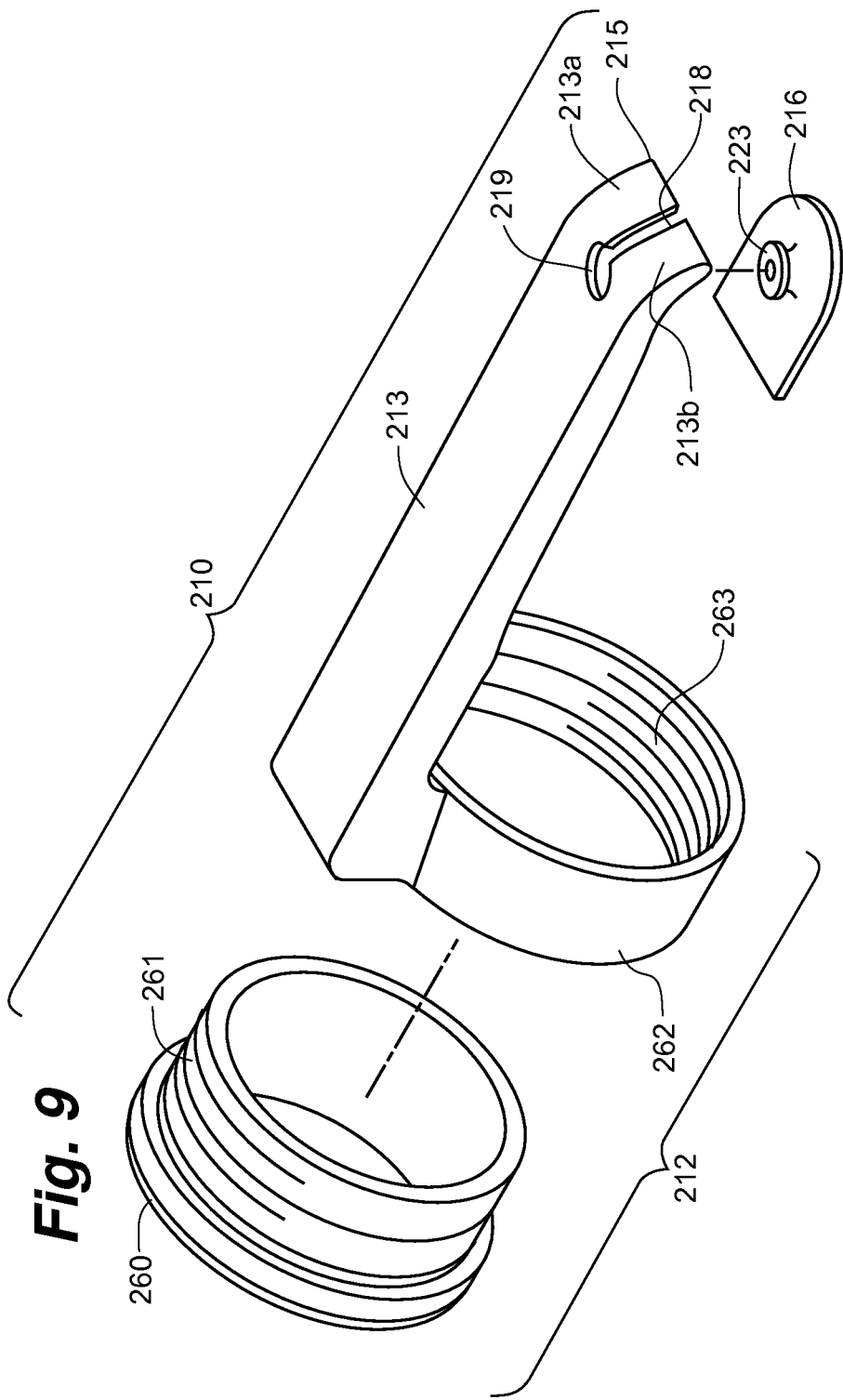
FIG. 9 is an exploded top perspective view of the exemplary embodiment of FIG. 7.
Figure 10:
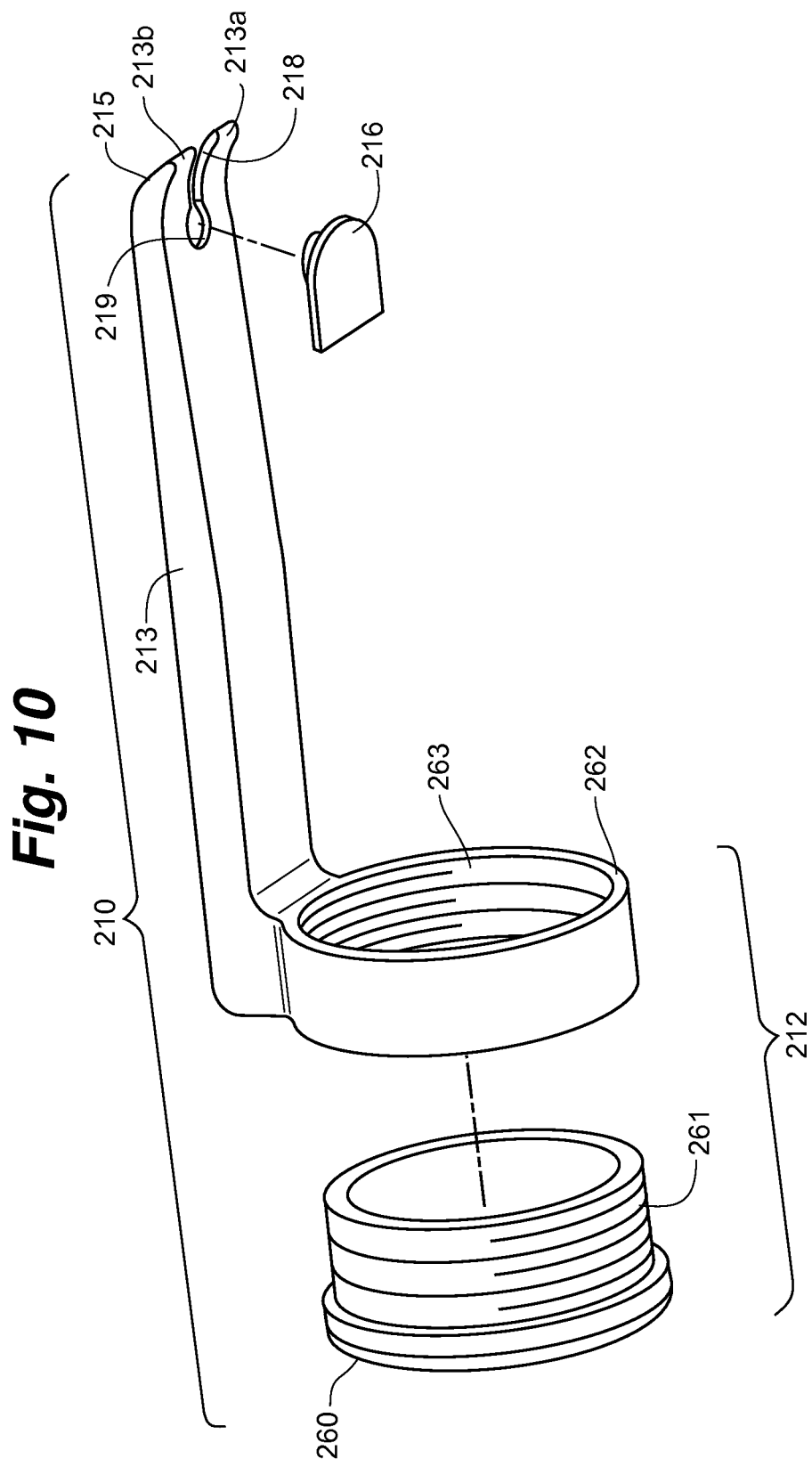
FIG. 10 is an exploded bottom perspective view of the exemplary embodiment of FIG. 7.

Referring now to FIGS. 9 and 10, the finger splint 210 may also have a slit 218 connected to the aperture 219 and extending to the distal end 215, defining a first side 213a and a second side 213b on the distal end 215 of the extension member 213. The slit 218 allows the diameter of the aperture 219 to be increased when a rotatable axial force is applied proximate the slit 218, pushing the first and second sides 213a, 213b on the distal end 215 away from each other. The slit 218 also allows the diameter of the aperture 219 to be increased. In certain aspects, the protruding portion 223 may have a diameter that is larger than the diameter of the aperture 219, such that the slit 218 allows enough flexibility for the size of the aperture 219 to be increased to allow the insertion of at least a part of the protruding portion 223 into the aperture 219.

In certain aspects, the extension member 213 and ring element 212 may be integral and attached to each other. In other certain aspects, the ring element 212 and the extension member 213 may not be integral and may, instead, be separate pieces that may be fixedly and/or adjustably attached to each other, as shown in an embodiment of a finger splint 210 in FIGS. 9-10. Extension member 213 and ring element 212 may be attached to each other through an adjustment mechanism so that the distance between the distal end 215 of the extension member 213 and the ring element 212 may be adjusted where, e.g., the extension member 213 attaches to the ring element 212. This adjustment mechanism allows the finger splint 210 to compensate for fingernail growth, preferably when the protruding portion 223 of the attachment element 216 is operably engaged with the aperture 219 of the extension member 213. As the fingernail grows and the attachment element 216 remains adhered to the fingernail, the threaded male section 260 may be unscrewed from the threaded female section 262 to account for fingernail growth and allow the user to more comfortably fit into finger splint 210.

Figure 11:
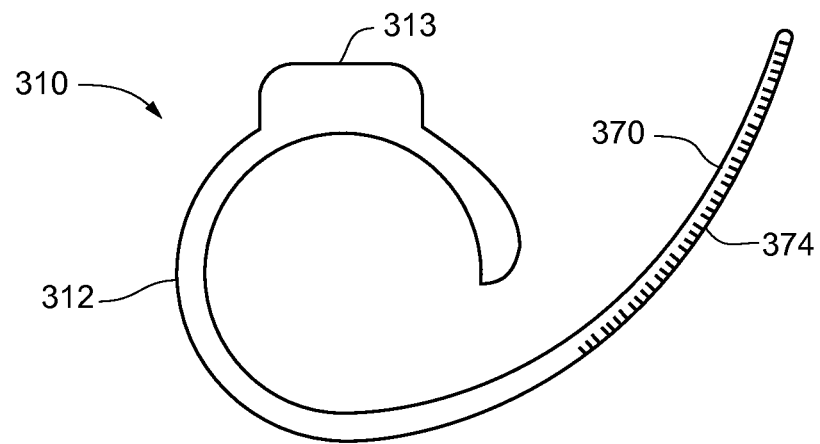
FIG. 11 is an end view of another exemplary embodiment of a splint according to the present invention.
Figure 12:
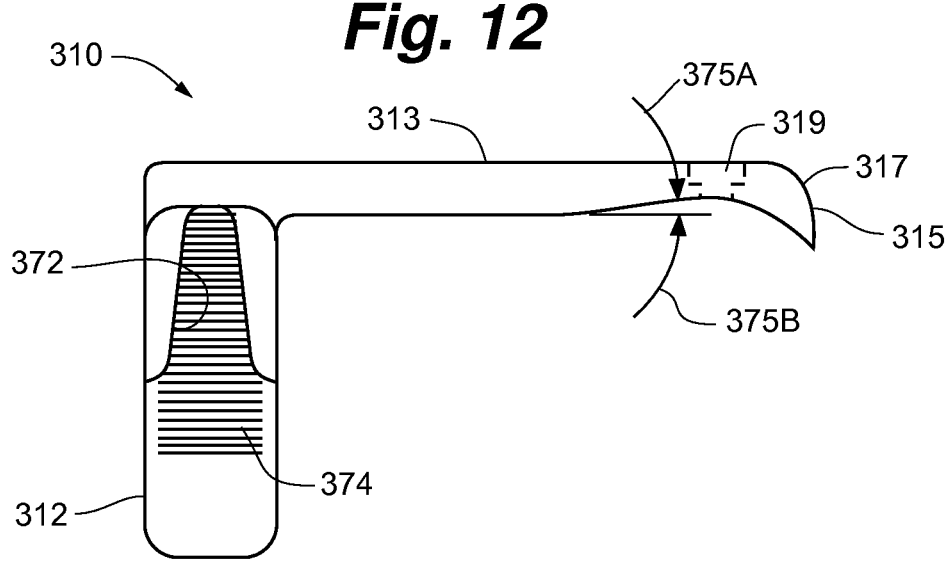
FIG. 12 is a side view of the splint of FIG. 11.

Another exemplary embodiment of a finger splint according to the present invention is depicted in FIGS. 11 and 12, with FIG. 11 being a view taken along the axis of the extension member 313 of the finger splint 310 and FIG. 12 being a side view of the finger splint 310. The finger splint 310 includes a ring element 312 that includes a tab 370 that fits within a slot 372 to form a closed loop so that the ring element 312 can be retained in place on a finger. The tab 370 may preferably include a ratchet mechanism that includes slotted surface 374 that cooperates with a pawl (not shown) located in the slot 372 to prevent removal of the tab 370 from the slot 372.

In essence, the tab 370 and slot 372 function in the manner of a cable tie. In some embodiments, the ratchet mechanism may include structure that allows for release of the pawl (if, e.g., the tab 370 is pulled too far through the slot 372). As seen in FIG. 12, the portion of the tab 370 may be removed after the ring element 312 is in a select position. Although the tab 370 is depicted as an integral component with the ring element 312, the ring element 312 may be provided separately from the tab 370 such that the tab 370 is provided in the form of a discrete article (e.g., a cable tie) that cooperates with the ring element 312 (e.g., is fitted in a slot, channel, through guides, etc.). Near the midsection of the extension member 313, i.e., between the distal end 315 and the ring element 312, the extension member 313 tapers as to form an angle 375 between 275A and 275B. The angle 375 may be, e.g., greater than zero degrees to about 25 degrees.

Referring now to FIGS. 13-15, in some aspects of the present invention, the attachment element 316 may comprise a protruding element 329 attached to an adhesive portion 325 that can adhere the attachment element 316 to a fingernail. The adhesive portion 325 may be a layer of material containing any suitable adhesive material or be comprised of the adhesive material itself, e.g., cyanoacrylate, epoxy, acrylic adhesives, etc. In certain aspects, the adhesive may be a pressure sensitive adhesive.

In certain aspects, the protruding element 329 comprises a protruding portion 323 connected to a base portion, which is shown in FIGS. 13-15 as dotted line 324 under an optional stabilizing layer 327. As shown in FIGS. 13-15, the stabalizing layer 327 overlays at least a portion of the base portion 324 while also allowing the protrusion of the protruding portion 323. The protruding portion 323 may protrude through the stabilizing layer 327, which is attached to the adhesive portion 325 to operably connect the protruding element 329 to the adhesive portion 325. The stabilizing layer 327 may comprise various different materials, such as a mesh, cloth, nylon, etc. In certain aspects of the present invention, the protruding element 329 is attached to the adhesive portion 325 without any stabilizing layer 327. In certain aspects, the base portion 324 is the same size as the adhesive portion 325, while in alternative aspects the base portion 324 can have various different sizes and shapes with respect to the adhesive portion 325. In other aspects, the base portion 324 is adhered directly to a fingernail 22 without any intermediate adhesive portion 325. The based portion 324 and/or adhesive portion 325 may be configured to have a concave shape, much like an acrylic nail, to correspond to the convex shape of fingernail 22 when applied thereto.

Referring now to FIGS. 14-15, in certain aspects of the present invention, attachment element 316 may also contain a removable layer 339 covering the adhesive portion 325 of attachment element 326. As shown in FIG. 15, which shows removable layer 339 partially removed to partially expose the adhesive portion 325, the removable layer 339 maintains the integrity of the adhesive portion 325 until the attachment element 316 is to be applied to the fingernail 22 of the patient. Once the removable layer 339 is completely removed from the adhesive portion 325, the adhesive portion 325 of the attachment element 316 may be adhered to a fingernail 22.

In certain aspects, the protruding element 323 has an intermediately located extension section 330 between the distal end 331 and the proximal end 332, the intermediately located extension section 330 having a smaller diameter than the diameter of the distal end 331. When the distal end 331 of the protruding element 329 of the attachment element 316 is pressed into the aperture (i.e., reference numerals 19, 219, 319 of the preceding exemplary embodiments) of the extension member (i.e., reference numerals 13, 213, 313 of the preceding exemplary embodiments), the distal end 331 passes through the aperture and the intermediately located extension section 330 is operably engaged within the aperture such that the outer perimeter of the intermediately located section 330 operably engages within the inner cross sectional portion of the aperture located on the extension member.

In certain aspects of the present invention, as shown in FIG. 15, the intermediately located extension section 330 between the distal end 331 and the proximal end 332 has a smaller diameter than the diameter of the distal end 331 defining a shoulder portion 328 proximate the distal end 331. The protrusion element 329 may comprise a rigid material with enough pliability or flexibility such that the shoulder portion 328 may be fitted within an aperture having a smaller diameter than the diameter of the shoulder portion 328 to operably engage the attachment element 316 with the extension member 313. In certain aspects, shoulder portion 328 is mutually exclusive of the diameter of the distal end 331, which in such cases the shoulder portion 328 still has a diameter larger than the diameter of the intermediately located extension section 330.

When the distal end 331 of the protruding portion 323 is pressed into the aperture of the extension member, the distal end 331 passes through the aperture and the intermediately located extension section 330 is operably engaged within the aperture such that the outer perimeter of the intermediately located section 330 operably engages with the inner cross sectional portion of the extension member 313 proximate the aperture 319. The shoulder portion 328 may also operably engage the top side of the extension member 313 or a recessed portion of the extension member proximate the aperture 319. When the distal end 331 of the protruding element 329 is inserted within the aperture 319, the mechanical fitting by the inner cross sectional portion of the extension member 313 proximate the aperture 319 encompassing the protruding portion 323 (as shown in the embodiment of FIG. 4) and/or at least a portion of the extension member located between the shoulder portion 328 and the base portion 324 mechanically couples the attachment element 316 to the extension member 313. The mechanical coupling prevents the attachment element 316 from being inadvertently detached from the extension member 313.

Referring now generally to FIGS. 16-21, top plane views of various extension member configurations proximate the distal end 415 are shown. As shown in FIG. 16, the distal end 415 of extension member 413 may have an aperture 419 with a slit 418 extending from the aperture 419 to the distal end 415. The extension member 413 proximate the aperture 419 may also have a recessed portion having a larger diameter than the diameter of the aperture thereby defining a shoulder portion 411. During use, the shoulder portion 411 may operably engage the shoulder portion 328 of the protruding element 329 when the attachment element is operably coupled to the extension member 413.

The slit 418 located between the aperture 419 and the distal end 415 defines a first side 413a and a second side 413b of the extension member 413 proximate the distal end 415. The diameter of the aperture 419 is capable of being increased when a rotatable axial force is applied proximate the slit 418, the rotatable axial force pushing first side 413a and second side 413b in a direction away from each other. When the diameter of the aperture 419 is increased, the radial force applied by the inner cross sectional portion of the extension member 313 proximate the aperture 319 onto the protruding portion 323 is relieved allowing the attachment element 413 to be detached from the extension member 413. In the instances where the attachment element contains a shoulder portion 318, the increased diameter of the aperture 419 also provides enough relief to enable the shoulder portion 318 to be removed.

In certain aspects of the present invention, the diameter of the shoulder portion 318 of the protrusion element 329 is smaller than the diameter of the aperture 419 of the extension member 413. As shown in FIGS. 17 and 18, the aperture 419 may be connected with a slot 440. In certain aspects, as shown in FIG. 17, the slot 440 may be located between the aperture 419 and the distal end 415. In certain aspects, as shown in FIG. 18, the aperture 419 may be located between the slot 440 and the distal end 415. The slot 440 may also contain a recessed portion defining an extension member shoulder portion 442. Although not shown, it is also contemplated that the extension member 413 has an aperture 419 with a first slot located between the aperture 419 and the distal end 415 and a second slot located such that the aperture 419 is between the second slot and the distal end 415.

During the mechanical coupling of the attachment element 316 to the extension member 413, the distal end 331 of the protrusion element 329 is capable of being inserted within the aperture 419 of the extension member 413 to operably couple the attachment element 316 to the extension member 413 in a stabilizing position. The intermediately located extension section 330 can operably engage and slide within the slot 440. For instance, as shown in FIG. 17, the intermediately located extension section 330 can operably engage and slide in a direction towards the distal end 415. Conversely, as shown in FIG. 18, the intermediately located extension section 330 can operably engage and slide in a direction away from the distal end 415. Thus, the slot 440, whether provided in the location of FIG. 17 or FIG. 18, allows for proper adjustment of the splint for different sized fingers and/or growth of a fingernail 18. The adjustment provided by the slot 440 also allows for some adjustment should the attachment element 316 be replaced on the fingernail 22 and the replacement attachment element 316 not be secured to the fingernail 22 in the same exact location.

In certain aspects, protruding element 330 contains shoulder portion 328 and the extension member 413 has a recessed portion proximate the slot 440 defining the extension member shoulder portion 442. When the distal end 331 is inserted within aperture 419, at least part of the shoulder portion 328 is capable of operably engaging at least a part of the extension member shoulder portion 442 such that there is a least a part of the extension member 413 located between the shoulder portion 328 and the base portion 324. During adjustment, the shoulder portion 328 can operably slide in the respective direction upon extension member shoulder portion 442.

In certain aspects of the present invention, the diameter of shoulder portion 328 is smaller than the diameter of aperture 419, but the slot 440 has a smaller width than the diameter of the shoulder portion 328. In these aspects, when the distal end 331 is inserted within aperture 419, the ring element 12 is placed into the proper position or otherwise adjusted such that at least part of the shoulder portion 328 operably engages at least a part of the extension member 413 or the extension member shoulder portion 442 when the intermediately located extension section 330 operably engages slot 440, such that there is a least a part of the extension member 413 located between the shoulder portion 328 and the base portion 324. During adjustment, the intermediately located extension section 330 operably slides within slot 440 in the respective direction with shoulder portion 328 operably sliding on the extension member 413 or the extension member shoulder portion 442 in the respective direction.

In certain aspects of the present invention, as shown in FIGS. 19 and 20, the extension member 413 may contain a slit 418. As shown in FIG. 19, the slit 418 may extend from the slot 440 to the distal end 415, or as shown in FIG. 20 extend from the aperture 419 to the distal end 415. In either situation, the slit 418 serves the function of allowing the size of the aperture 419 to be increased when a rotatable axial force is applied to operably release the attachment element from the extension member as previously discussed herein.

Referring now to FIG. 21, in certain aspects of the present invention, slit 418 may contain one or more intermediately located expansion key receiving apertures 450. In certain aspects, an expansion key can be inserted within the slit 418 with corresponding protruding components inserted within one or more receiving apertures 450. Preferably, the expansion key with one or more protruding components fits into receiving apertures 450 and can be rotated to apply a rotatable axial force with respect to first and second sides 413a, 413b so that the diameter of the aperture 419 can be increased to operably release the attachment element from the extension member.

Figure 22:
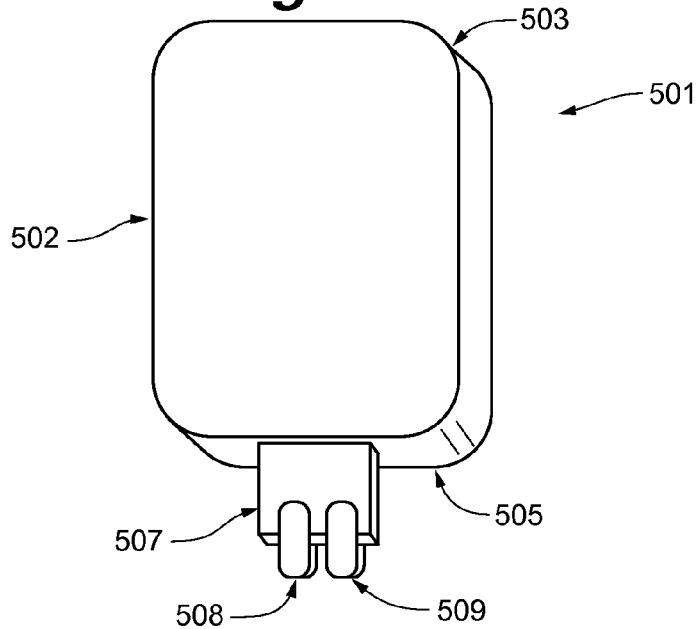
FIG. 22 is a perspective view of an exemplary expansion key for insertion within the receiving apertures of the slit in FIG. 21.
Figure 23:
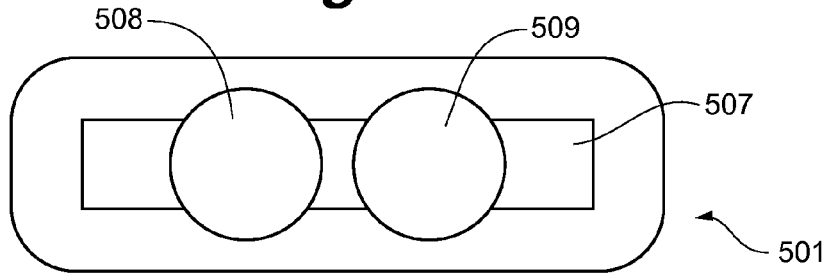
FIG. 23 is a bottom end view of the expansion key of FIG. 22.
Figure 24:
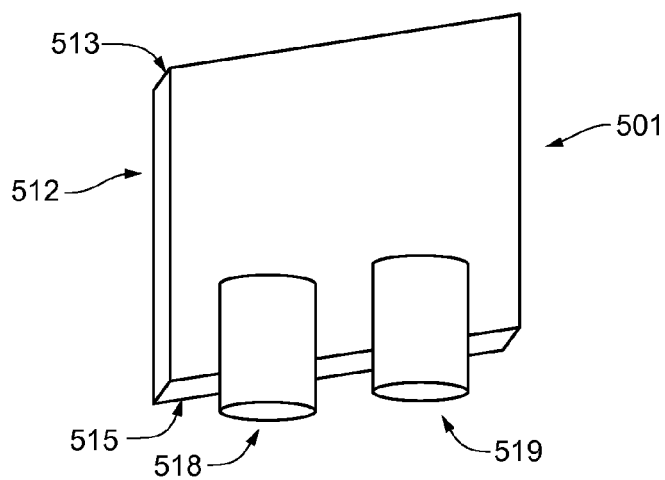
FIG. 24 is a perspective view of another exemplary expansion key for insertion within the receiving apertures of the slit in FIG. 21.

Exemplary embodiments of the expansion key that could be inserted and utilized in the slit 418 and receiving apertures 450 of the splint in FIG. 21 are shown illustrated in FIGS. 22-24. FIGS. 22 and 23 illustrate an exemplary embodiment of expansion key 501 for releasing an attachment element from the aperture of an extension member. Expansion key 501 includes a gripping portion 502 with top side 503 and bottom side 505, which allows user to get a firm grasp of expansion key 501 when inserting into the receiving apertures of a finger splint. Gripping portion 502 can be used to apply a rotatable axial force proximate the slit 418 of an extension member 413 so that the two sides of the extension member 413a, 413b proximate the slit 418 can be pushed away from each other, thereby releasing the attachment element from the extension member. Base 507 is connected to the bottom side 505 of the expansion key 501 and includes two protruding components 508 and 509. Protruding components 508 and 509 would fit into receiving apertures 450 so that the diameter of the aperture 419 is capable of being increased when a rotatable axial force is applied proximate the slit 418 of the extension member, pushing the two sides of the slit away from each other and thereby releasing the attachment element from the extension member.

FIG. 24 shows another exemplary embodiment of an expansion key 501. Expansion key 501 includes gripping portion 512 with top side 513 and bottom side 515. In this embodiment, two protruding components 518 and 519 are located on the bottom side 515 of the gripping portion 512 of expansion key 511. The protruding components 518 and 519 can be inserted into the receiving apertures 450 so that the diameter of the aperture 419 is capable of being increased when the rotatable axial force is applied.

As provided by the foregoing exemplary embodiments of the expansion key 501, the expansion key 501 can comprise various configurations and embodiments. In each instance, however, the key is inserted within slit 418 such that when the rotatable axial force is applied, the aperture 419 can be increased to release the mechanically attached attachment element from the extension member.

Figure 25:
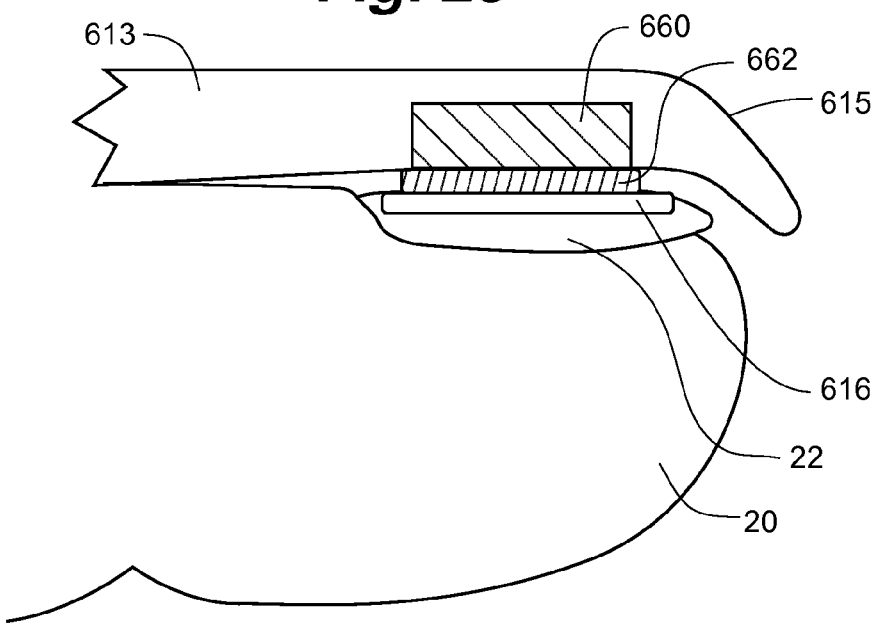
FIG. 25 is a side view of an exemplary extension member portion of a splint according to the present invention, the extension member having a stationary magnet that can magnetically attach to an attachment element having a magnet or magnetic attraction to the stationary magnet.
Figure 26:
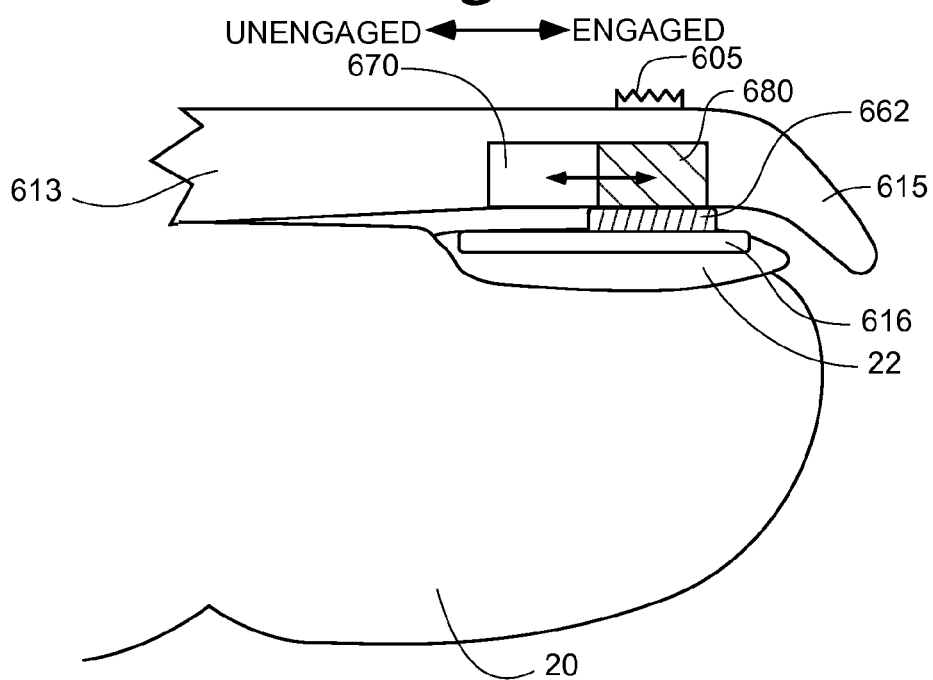
FIG. 26 is a side view of an exemplary extension member portion of a splint according to the present invention, the extension member having a slidable magnet that can magnetically attach to an attachment element having a magnet or magnetic attraction to the slidable magnet.
Figure 27:
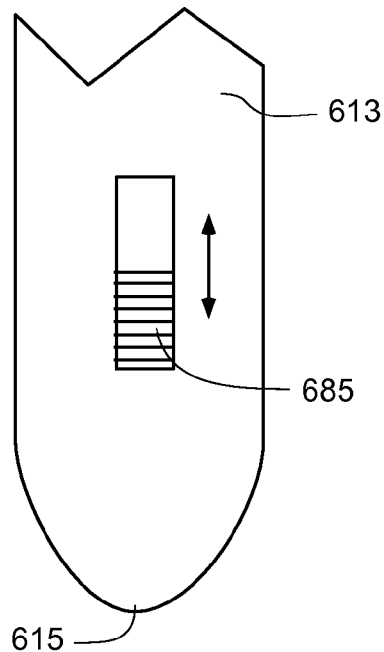
FIG. 27 is a top end view of the extension member having the slidable magnet of FIG. 26.

Referring now to FIG. 25-27, the splint utilizing a magnetic fastener system that can magnetically attach the finger attachment element to the extension member is illustrated. In certain aspects, as shown in FIG. 25 extension member 613 has a stationary magnet 660 located proximate the distal end 615. The stationary magnet 660 may include north end charge and/or a south end charge. The finger attachment element 616 may also contain a magnet 662 attached to a finger attachment portion, or alternatively contain a material that has a magnetic attraction to the stationary magnet 660. During use, the stationary magnet 660 magnetically attaches to a material in the finger attachment element 616, such as another magnet, a magnetized material, or other material that is has a magnetic interaction with the stationary magnet. In some aspects, the finger element 616 contains a magnet 662 while the extension member 613 contains a material that magnetically attaches to the magnet, such as a magnetized material, or other material that is has a magnetic interaction with the magnet. Such magnets may be comprised of permanent rare earth materials, such as neodymium, ($Nd_2Fe_{14}B$) or other materials known to one of ordinary skill in the art.

To operably engage the extension member 613 with the finger attachment element 616, the finger attachment element 616 is positioned proximal to the stationary magnet 660 such that there is enough of a magnetic attraction to operably engage the extension member 613 with the finger attachment element 616. To disengage the magnetic attraction, another larger magnet having an opposite polarity to the magnet in the finger attachment element 616 may be placed over the top of extension member 613 proximate the stationary magnet 660. Alternatively, finger 20 with magnetic attachment element 616 attached to the fingernail 22 can be moved in the direction away from stationary magnet 660 and extension member 613 so that there is no longer enough of a proximal magnetic attraction.

Referring now to FIGS. 26 and 27, in certain aspects of the present invention, the extension member 613 contains a housing 670 for holding a movable magnet 680. The movable magnet 680 within the housing 670 allows for the magnet 680 to be provided in an engaged or an unengaged position. In the engaged position, the magnet 680 is provided in a position such that there is a magnetic attraction between the magnet 680 of the extension member 613 and the magnet 662 of the finger attachment element 616 such that there is a magnetic coupling of the extension member 613 to the finger attachment element 616. In the unengaged position, the magnet 680 is slid within the housing 670 such there no longer is a magnetic attraction between the magnet 680 of the extension member 613 and the magnet 662 of the finger attachment element 616. In the unengaged position, there no longer is a magnetic coupling of the extension member 613 to the finger attachment element 616. One of ordinary skill in the art will appreciate that the poles of the magnets may be reversed within the extension member 613 and the finger attachment element 613 such that the North-South interaction can be utilized in different configurations.

In some aspects, the magnet 660 within housing 670 can be operably moved between the engaged and unengaged position by a portion of the magnet being exposed such that a tool can be used to toggle between the two positions, the magnet having a portion extending from the housing 670 that allows for the toggling, or a material attached to the magnet that allows for the toggling between the engaged and unengaged positions. As shown in FIGS. 26 and 27, a toggle switch coupled to the magnet is operable from the top surface of the extension member 613 over the top surface of the finger. One of ordinary skill in the art will appreciate the toggle switch may alternatively be located on the side of the extension member 613.

Figure 28:
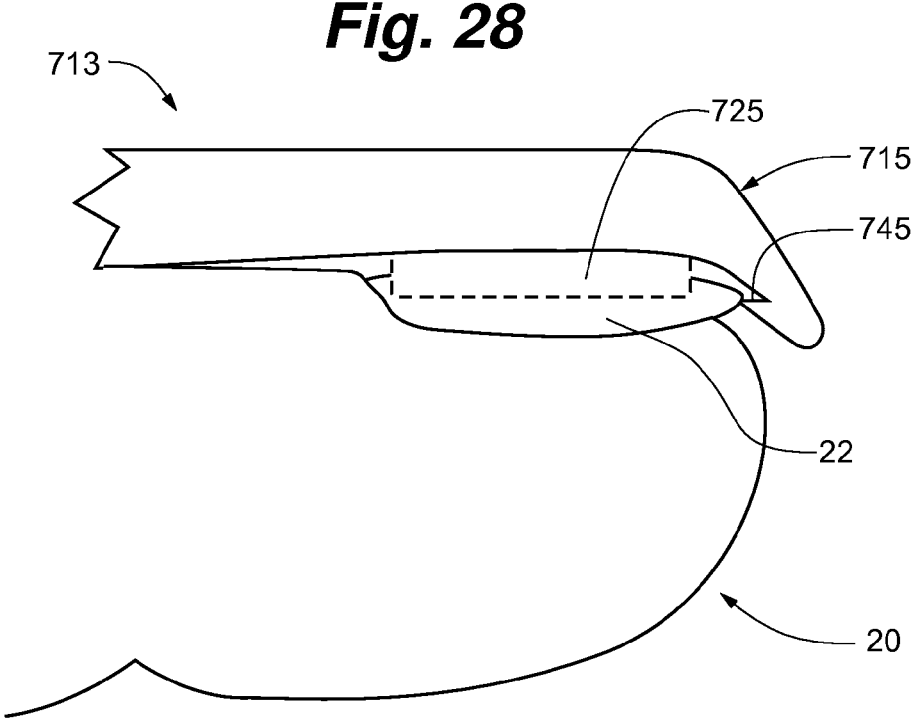
FIG. 28 is a side view of an exemplary extension member portion of a splint according to the present invention, the extension member having a fingernail groove to receive and hold the fingernail in place within the fingernail groove.

Referring now to FIG. 28, an exemplary embodiment of an extension member 713 with a grove slot 745 located on the distal end 715 of extension member 713. Groove slot 745 gives a finger splint user added support by allowing the fingernail 22 of finger 20 to fit into and rest into grove slot 745. The groove sot 745 also provides the ability to provide the finger 20 in hyperextension without necessarily attaching the fingernail 22 to the splint 10. Instead, the groove slot 745 provides enough force on the bottom of the fingernail 22. In certain aspects, an adhesive portion 725 may be applied to the fingernail 22 such that the fingernail 22 can be attached to the extension member 713.

Figure 31:
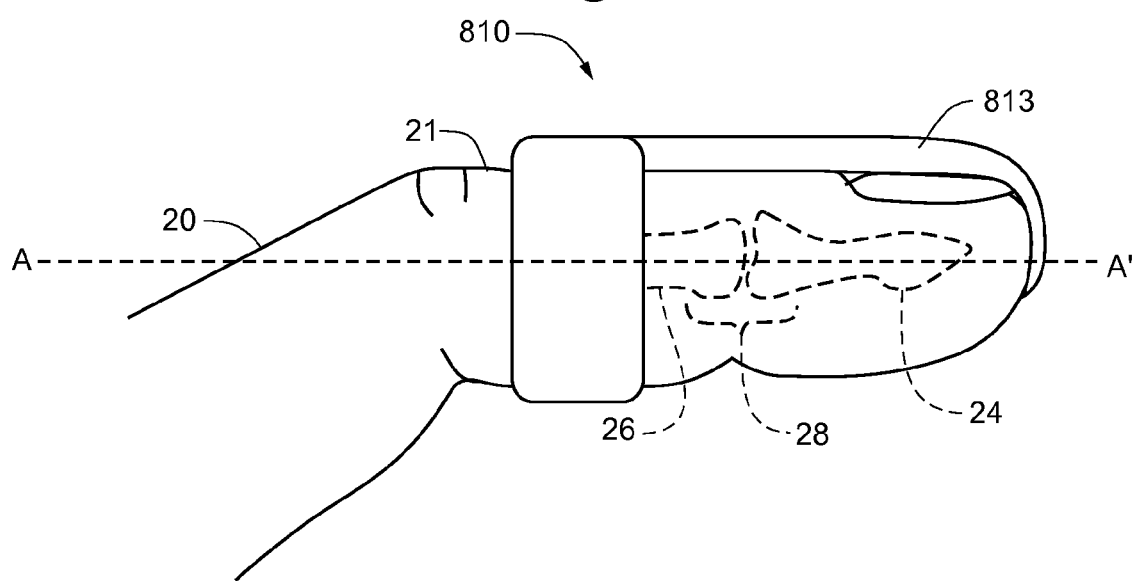
FIG. 31 is a side view of the splint of FIG. 29 in place on the DIP joint of a finger, the flexible ring portions bent at least partially around the finger as a central axis to form the ring element, and the extended overlay material past the distal end of the extension member operably engaging at least a portion of the tip of the finger.

Referring now to FIGS. 29-31, in certain aspects of the present invention, the splint 810 is provided in a substantially flat configuration prior to being used in the treatment of a finger injury, which allows the splint 810 to be packaged in a flat configuration. The flat configuration also allows for the splint 810 to be manufactured in a stamping process, such that the splint 810 is stamped in a "T-shaped" configuration. The T-shaped configuration may also be obtained by other processes, such as injection molding.

In certain aspects, the splint 810 comprises a first bendable or flexible ring portion 812a and a second bendable or flexible ring portion 812b (shown in FIG. 29 as dotted beneath a top overlay material 810) that is substantially perpendicular to an extension member 813 (also shown dotted). Each ring portion 812a, 812b is capable of being bent at least partially into an arcuate shape around a central axis (illustrated by dotted lines B and B' around dotted line A-A' in FIGS. 29 and 30), the two ring portions 812a, 812b bent into arcuate shapes around the central axis forming a ring element configuration. As illustrated in FIG. 31, the central axis being the finger 20, particularly the distal phalanx 24 and middle phalanx 26 of the finger 20, when the splint is used in the treatment of a finger injury.

In both the flat configuration and the bent configuration when the first and/or second ring portions 812a, 812b are bent around a central axis, the first and second ring portions 812a, 812b are attached to the proximal end 814 of an extension member 813. The extension member 813 also has a distal end 815 located distally from the ring portions 812a, 812b. As shown best in FIG. 31, the splint 810 may also have an attachment element 816 capable of operably coupling the extension member 813 to a fingernail 22 when the ring portions 812a, 812b are held at least partially around the finger 20 in a ring element configuration. In certain aspects, as previously discussed with respect to other embodiments, the attachment element 816 may have a protruding portion that operably engages with an aperture towards the distal end of the extension member.

In certain aspects, an overlay material 810 is provided over the bendable ring portions 812a, 812b and/or the extension member 813. In some aspects, the bendable ring portions 812a, 812b comprise a relatively thin and flexible material while the extension member 813 is a relatively thick material that provides more rigidity. In some aspects, the bendable ring portions 812a, 812b and extension member 813 comprise a plastic material known to one of ordinary skill in the art to provide the proper flexibility or rigidity (i.e., polyethylene, polypropylene, PEEK, or other stiff and pliable plastic materials). In some aspects, the overlay material 810 is directly connected to the material of the ring portions 812a, 812b and/or extension member 813 by overlay molding. In some aspects, the overlay material is connected to the material of the ring portions 812a, 812b and/or extension member 813 by an intermediate adhesive. In some aspects, the overlay material 810 comprises a nylon material, in other aspects a wicking material, such as Gortex®, that facilitates the removal of moisture from the skin. In some aspects, the overlay material 810 is an adhesive material, such that the adhesive material may be adhered to itself to form the ring element configuration.

In certain aspects, the ring portions 812a, 812b are bent into a ring element configuration at least partially around the finger and held in the ring element configuration by the overlay material 820 adhering to itself. In some aspects, the overlay material 820 that is not covering the ring portions 812a, 812b and/or extension member 813 only contains an adhesive material proximate the distal end areas 822a, 822b of the bendable ring portions 812a, 812b, such that the overlay material 820 can be adhered to itself and maintain the ring portions 812a, 812b in a ring element configuration, such as shown in FIG. 31. The overlay material 820 may contain other means for fastening the ring portions 812a, 812b to retain the ring portions 812a, 812b in a ring element configuration during the treatment of a finger injury, such that the ring portions 812a, 812b extend at least partially around the finger 20. For instance, in some aspects, the overlay material 820 may contain hook and fasten type material proximate the distal end areas 822a, 822b of the bendable ring portions, such as Velcro®.

In some aspects of the present invention, the overlay material 820 extends at least partially the length of the extension element 813, in other aspects the entire length of the extension element 813, and in other aspects a length exceeding the extension element 813. In some aspects, the overlay material 820 is wider than the width of the extension element 813, such that the overlay material 820 can operably interact with the finger. In some aspects, the portion of the overlay material 820 that is wider than the extension element 813 contains an adhesive material that allows the overlay material 820 to be adhered to the finger 20 at a location intermediate the proximal end 814 and the distal end 815 of the extension member 813. In some aspects, the overlay material 820 extends over the distal end 815 of the extension element 813 and contains an adhesive portion proximately located, such that the adhesive overlay material 820 can attach at least partially to the finger tip, such as shown in FIG. 31.

In certain aspects, besides the splint 810 having an overlay material 820 over the ring portions 812a, 812b, the ring portions 812a, 812b may include an inner portion that comes in contact with the skin that is a different material than the remaining portion of the ring portions 812a, 812b. In some aspects, the inner portion and the main ring portions 812a, 812b comprise different materials. In some aspects, the inner portion includes a material that has a shore hardness that is less than the outer portion. In some aspects, the material of the inner portion is directly connected to the main ring portions 812a, 812b by overlay molding, while in other aspects the two different materials are connected by an intermediate adhesive. In some aspects, the inner portion comprises a soft cushion-like material, such as a foam, cloth material, gel or the like. In some aspects, the inner portion comprises a wicking material, such as Gortex®, that facilitates the removal of moisture from the skin.

In still other aspects, the inner portion of the ring portions 812a, 812b that contact the finger when configured into a ring element may comprise a material that extends beyond the distal ends of the ring portions 812a, 812b, such that the inner extending material may be used to retain the ring portions 812a, 812b in the ring element configuration. The inner extending material may contain other means for fastening the ring portions 812a, 812b to retain the ring portions 812a, 812b in a ring element configuration during the treatment of a finger injury, such that the ring portions 812a, 812b extend at least partially around the finger 20. For instance, in some aspects, the inner extending material may contain hook and fasten type material proximate the distal end areas 822a, 822b of the bendable ring portions, such as Velcro®.

In another aspect, the present invention may provide a method of restraining a finger 20 as shown in FIG. 31, the method including locating a splint 810 on a finger 20, wherein the splint 810 includes flexible ring portions 812a, 812b, the flexible ring portions 812a, 812b capable of being bent into a ring element that is capable of being positioned proximally from the distal interphalangeal joint and an attachment element 816 positioned adjacent a fingernail 24 of the finger 20, with an extension member 813 connecting the attachment element 816 to the ring portions 812a, 812b forming the ring element configuration. In some aspects, the splint 810 comprises an overlay material 820, the overlay material 820 containing means for retaining the flexible ring portions 812a, 812b in a ring element configuration. In other aspects, the splint 810 comprises an inner extending material proximate the ring portions 812a, 812b, the inner extending material containing means for retaining the flexible ring portions 812a, 812b in a ring element configuration. In some aspects, the overlay material 820 also extends over the width of the extension member 813 such as to hold the extension member to an intermediate portion of the finger and/or extending over the distal end 815 of the extension member 814 such that the overlay material 810 may be at least partially attached to the finger tip. In some other aspects, the overlay material is provided between the extension member 813 and the finger 20, such as to hold the extension member to an intermediate portion of the finger and/or extending over the distal end 815 of the extension member 814, such that the overlay material 820 may be at least partially attached to the finger tip, when the overlay material contains an adhesive material that is attachable to the finger and/or finger tip.

Although the exemplary embodiments described herein depict the finger splint utilized with a finger, the finger splint may be used on other appendages, such as, but not limited to, toes on a foot. Further, although the exemplary embodiments described herein depict the finger splint utilized with the distal interphalangeal joint, the finger splint may be used on other joints, such as, but not limited to, the proximal interphalangeal joint.

The complete disclosure of the patents, patent documents, and publications cited in the Background, the Summary, the Detailed Description of Exemplary Embodiments, and elsewhere herein are incorporated by reference in their entirety as if each were individually incorporated. Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

The invention claimed is:

1. A finger splint for use in the treatment of finger injuries, the splint comprising:
  a first flexible ring portion and a second flexible ring portion, the first flexible ring portion capable of being bent around a central axis to form a first arcuate ring portion and the second flexible ring portion capable of being bent around the central axis to form a second arcuate ring portion, the first and second arcuate ring portions capable of at least partially fitting around a finger at a location proximal to the distal interphalangeal (DIP) joint to form a ring element configuration;
  an extension member comprising a proximal end attached to the first and second flexible ring portions and a distal end located distally from the first and second flexible ring portions;
  an attachment element overlaying and attachable to a distal portion of the extension member proximate the distal end of the extension member, wherein the attachment element comprises an adhesive that is capable of attaching the distal end of the extension member only to a fingernail when the first and second flexible ring portions are positioned at least partially around the finger and the extension member is configured to be positioned over a top surface of the finger; and
  an overlay material proximate the distal end of the extension member having an adhesive portion capable of attaching at least partially to a finger tip of the finger;
  wherein the extension member extends from the proximal end to the distal end substantially perpendicular to a first plane defined by the first and second flexible ring portions.

2. The finger splint of claim 1, further comprising an overlay material connected to at least a portion of the first flexible ring portion.

3. The finger splint of claim 2, wherein the overlay material comprises a means for retaining the first and second flexible ring portions in the ring element configuration.

4. The finer splint of claim 2, wherein the overlay material comprises a portion that extends beyond the first flexible ring portion.

5. The finger splint of claim 4, wherein the portion of the overlay material that extends beyond the first flexible ring portion comprises at least a portion comprising an adhesive material, the adhesive material capable of being connected to the second flexible ring portion to retain the first and second flexible ring portions in the ring element configuration.

6. The finger splint of claim 5, wherein the overlay material connected to at least a portion of the first flexible ring portion is positioned over an outer surface of the first flexible ring portion, such that the first flexible ring portion is located between the overlay material and the finger.

7. The finger splint of claim 5, wherein the overlay material connected to at least a portion of the first flexible ring portion is positioned between the first flexible ring portion and the finger.

8. The finger splint of claim 2, further comprising an overlay material connected to at least a portion of the second flexible ring portion.

9. The finger splint of claim 8, wherein a portion of the overlay material that extends beyond the first flexible ring portion comprises at least a portion comprising an adhesive material, the adhesive material capable of being connecting to the overlay material connected to at least a portion of the second flexible ring portion to retain the first and second flexible ring portions in the ring element configuration.

10. The finger splint of claim 1, further comprising an overlay material connected to at least a portion of the first flexible ring portion, at least a portion of the second flexible ring portion, at least a portion of the extension member, or combinations thereof.

11. The finger splint of claim 10, wherein the overlay material is connected to at least a portion of the extension member, and the overlay material having a portion that extends beyond the extension member.

12. The finger splint of claim 11, wherein the portion of the overlay material that extends beyond the extension member is capable of being attached to at least a portion of a tip of the finger.

13. The finger splint of claim 1, wherein the extension member comprises an aperture proximate the distal end, and the attachment element comprises a protruding portion capable of operably engaging with the aperture to attach the attachment element to the extension member.

14. The finger splint of claim 13, wherein a size of the aperture is smaller than a size of the protruding portion, such that the aperture and protruding portion provide a mechanical slip fitting to mechanically fasten the attachment element to the extension member.

15. The finger splint of claim 13, further comprising a slit located between the aperture and the distal end of the extension member.

16. A finger splint for use in the treatment of finger injuries, the splint comprising:
  a first and second ring portion comprising a flexible adhesive material, the first and second ring portions capable of being bent towards each other at least partially around a finger at a location proximal to the distal interphalangeal (DIP) joint to form a ring element configuration;
  an extension member comprising a proximal end extending from the first and second ring portions to a distal end located distally from the first and second ring portions;
  an attachment element overlaying a distal portion of the extension member proximate the distal end of the extension member, wherein the attachment element comprises an adhesive that is capable of attaching the distal end of the extension member only to a fingernail when the first and second ring portions are positioned at least partially around the finger to form the ring element configuration and the extension member is configured to be positioned over a top surface of the finger; and an overlay material connected to at least a portion of the first ring portion, at least a portion of the second ring portion, at least a portion of the extension member, or combinations thereof;

wherein at least a portion of the extension member and at least a portion of the first and second ring portions are within a first plane prior to the first and second ring portions being bent around the finger to form the ring element configuration; and wherein the extension member extends from the proximal end to the distal end substantially perpendicular to a second plane defined by the first and second ring portions formed into the ring element configuration.

17. The finger split of claim 16, wherein the overlay material connected to at least a portion of the first ring portion also comprising an extension portion that extends beyond the first ring portion, and the extension portion comprising an adhesive material to operably retain the first and second ring portions in the ring element configuration.

18. The finger splint of claim 17, wherein the adhesive material directly connects the overlay material of the first ring portion to the overlay material of the second ring material to operably retain the first and second ring portions in the ring element configuration.

19. The finger splint of claim 16, wherein the overlay material is connected to at least a portion of the extension member, the overlay material connected to at least a portion of the extension member also comprising an extension portion that extends beyond the distal end of the extension member, and the extension portion comprising an adhesive material to operably attach to at least a portion of a tip of the finger.

20. The finger splint of claim 19, wherein the overlay material is connected to at least a portion of the first ring portion and at least a portion of the second ring portion, the overlay material connected to at least a portion of the first ring portion also comprising an extension portion that extends beyond the first ring portion, and the extension portion that extends beyond the first ring portion comprising an adhesive material to operably connect the overlay materials of the first and second ring portions to retain the first and second ring portions in the ring element configuration.

21. The finger splint of claim 16, further comprising a flexible ring portion comprising a plastic material having a first end, a second end, and an intermediate area, the first end connected to the first ring portion, the second end connected to the second ring portion, and the intermediate area connected to the proximal end of the extension member, wherein the first and second ends are capable of being bent towards each other at least partially around the finger at the location proximal to the distal interphalangeal (DIP) joint when the first and second ring portions are bent towards each other to form the ring element configuration.

22. The finger splint of claim 16, wherein the flexible adhesive material is a pressure sensitive adhesive.

23. The finger splint of claim 16, further comprising the flexible adhesive material located between the attachment element and the extension member.

24. The finger splint of claim 23, wherein the overlay material comprises an adhesive material connected to at least a portion of the first ring portion, at least a portion of the second ring portion, and at least a portion of the extension member.

25. The finger splint of claim 16, wherein the overlay material is connected to the distal end of the extension member and having an adhesive portion capable of attaching at least partially to a finger tip of the finger.

26. A finger splint for use in the treatment of finger injuries, the splint comprising:
   a ring element configured to fit at least partially around a finger at a location proximal to the to the distal interphalangeal (DIP) joint;
   an extension member having a proximal end attached to the ring element, a distal end located distally from the ring element, and an aperture proximate the distal end of the extension member;
   an attachment element having a protruding portion capable of operably engaging within the aperture on the extension member; and
   an overlay material proximate the distal end of the extension member having an adhesive portion capable of attaching at least partially to a finger tip of the finger;
   wherein the attachment element is capable of operably coupling the extension member to a fingernail of the finger when the ring element is positioned at least partially around the finger and the protruding portion is operably engaged within the aperture of the extension member.

27. The finger splint of claim 26, wherein the ring element comprises a first ring tab portion and a second ring tab portion, the first and second ring tab portions comprising a flexible material allowing the first and second ring tab portions to be operably bent around a finger axis.

* * * * *